United States Patent
Olsen et al.

(10) Patent No.: US 10,280,426 B2
(45) Date of Patent: *May 7, 2019

(54) METHOD FOR STABLE GENE-AMPLIFICATION IN A BACTERIAL HOST CELL

(71) Applicant: Novozymes A/S, Bagsvaerd (DK)

(72) Inventors: Carsten Olsen, Bagsvaerd (DK); Michael Dolberg Rasmussen, Vallensbaek (DK)

(73) Assignee: Novozymes A/S, Bagsvaerd (DK)

( * ) Notice: Subject to any disclaimer, the term of this patent is extended or adjusted under 35 U.S.C. 154(b) by 85 days.

This patent is subject to a terminal disclaimer.

(21) Appl. No.: 15/252,548

(22) Filed: Aug. 31, 2016

(65) Prior Publication Data
US 2016/0362698 A1    Dec. 15, 2016

Related U.S. Application Data

(60) Division of application No. 14/180,975, filed on Feb. 14, 2014, now Pat. No. 9,458,468, which is a continuation of application No. 12/712,537, filed on Feb. 25, 2010, now Pat. No. 8,685,653, which is a continuation of application No. 10/575,697, filed as application No. PCT/DK2004/000750 on Oct. 29, 2004, now Pat. No. 7,700,322.

(60) Provisional application No. 60/518,916, filed on Nov. 10, 2003.

(30) Foreign Application Priority Data
Oct. 31, 2003    (DK) .................................. 2003 01624

(51) Int. Cl.
| | |
|---|---|
| *C12N 9/10* | (2006.01) |
| *C12N 9/38* | (2006.01) |
| *C12N 15/75* | (2006.01) |
| *C12P 21/00* | (2006.01) |

(52) U.S. Cl.
CPC ............ *C12N 15/75* (2013.01); *C12N 9/1007* (2013.01); *C12N 9/2471* (2013.01); *C12P 21/00* (2013.01); *C12Y 201/01014* (2013.01); *C12Y 302/01023* (2013.01)

(58) Field of Classification Search
None
See application file for complete search history.

(56) References Cited

U.S. PATENT DOCUMENTS

| | | |
|---|---|---|
| 6,762,040 B2 | 7/2004 | Rasmussen |
| 7,700,322 B2 | 4/2010 | Olsen et al. |
| 8,685,653 B2 | 4/2014 | Olsen et al. |
| 9,458,468 B2 * | 10/2016 | Olsen ..................... C12N 15/75 |

FOREIGN PATENT DOCUMENTS

| | | |
|---|---|---|
| EP | 0 972 838 A1 | 1/2001 |
| WO | 94/14968 A1 | 7/1994 |
| WO | 97/09435 A1 | 3/1997 |
| WO | 2001/90393 A1 | 11/2001 |
| WO | 2002/00907 A1 | 1/2002 |

OTHER PUBLICATIONS

Glenting et al., "A plasmid selection system in Lactococcus lactis and its use for gene expression in L. factis and Human kidney fibroblasts", Applied and Environmental Microbiology, vol. 68, No. 10, pp. 5051-5056 (2002).

Mollet et al., "Directed genomic integration, gene replacement, and integrative gene expression in *Streptococcus thermophilus*", Journal of Bacteriology, vol. 175, No. 14 pp. 4315-4324 (1993).

\* cited by examiner

*Primary Examiner* — Anand U Desai
(74) *Attorney, Agent, or Firm* — Eric J. Fechter

(57) ABSTRACT

A bacterial host cell is disclosed including at least two copies of an amplification unit in its genome, the amplification unit including: i) at least one copy of a gene of interest, and ii) an expressible conditionally essential gene, wherein the conditionally essential gene is either promoterless or transcribed from a heterologous promoter having an activity substantially lower than the endogenous promoter of the conditionally essential gene, and wherein the conditionally essential gene if not functional would render the cell auxotrophic for at least one specific substance or unable to utilize one or more specific sole carbon source; methods for producing a protein using the cell of the invention, and methods for constructing the cell of the invention.

16 Claims, No Drawings
Specification includes a Sequence Listing.

SEQUENCE LISTING

<160> NUMBER OF SEQ ID NOS: 17

<210> SEQ ID NO 1
<211> LENGTH: 35
<212> TYPE: DNA
<213> ORGANISM: artificial sequence
<220> FEATURE:
<223> OTHER INFORMATION: Synthetic construct

<400> SEQUENCE: 1
aataataaag atctggagga gaaacaatga caacc                              35

<210> SEQ ID NO 2
<211> LENGTH: 33
<212> TYPE: DNA
<213> ORGANISM: artificial sequence
<220> FEATURE:
<223> OTHER INFORMATION: Synthetic construct

<400> SEQUENCE: 2
aaataataag atctaaatta tactagctgt gtc                                33

<210> SEQ ID NO 3
<211> LENGTH: 39
<212> TYPE: DNA
<213> ORGANISM: artificial sequence
<220> FEATURE:
<223> OTHER INFORMATION: Synthetic construct

<400> SEQUENCE: 3
attttatagg atcccgctga ttcattttct tctgcgaac                          39

<210> SEQ ID NO 4
<211> LENGTH: 48
<212> TYPE: DNA
<213> ORGANISM: artificial sequence
<220> FEATURE:
<223> OTHER INFORMATION: Synthetic construct

<400> SEQUENCE: 4
gaattccatc gcactggacg acattttcag gtcgattctc ggaaatcc                48

<210> SEQ ID NO 5
<211> LENGTH: 50
<212> TYPE: DNA
<213> ORGANISM: artificial sequence
<220> FEATURE:
<223> OTHER INFORMATION: Synthetic construct

<400> SEQUENCE: 5
cccgaggcct ttcaggcccg caaacaatat ggttgaagcc gcaaaacagg              50

<210> SEQ ID NO 6
<211> LENGTH: 39
<212> TYPE: DNA
<213> ORGANISM: artificial sequence
<220> FEATURE:
<223> OTHER INFORMATION: Synthetic construct

<400> SEQUENCE: 6
ataataatgg taccatattg atgtgacact tgaagttgc                          39

<210> SEQ ID NO 7
<211> LENGTH: 7311
<212> TYPE: DNA
<213> ORGANISM: artificial sequence
<220> FEATURE:
<223> OTHER INFORMATION: Synthetic construct

<400> SEQUENCE: 7

```
cttggagggc caagcgatgt gccagagcta aaagaagcag tgaaaaacgc agtgaaaaac      60
ggagtgcttg tcgtttgtgc agcgggaaat gaaggtgacg gcgacgaacg cacagaagag     120
ctttcctacc ccgcagctta taatgaagtg attgcagttg gatctgtttc tgtagcgcga     180
gaattatcag aattttctaa cgcgaataaa gagattgacc ttgtggcacc aggagaaaac     240
atcttatcca cccttcccaa caagaagtac ggtaagctga ccggcacttc aatggctgcc     300
cctcatgtca gcggtgcgct tgctttaatc aaaagctatg aagaagaatc atttcaaaga     360
aagctttctg aatctgaggt tttcgcacag ctaatccgca ggacacttcc tcttgatatt     420
gcaaaaacgc tggcaggcaa tggattcctg tatttaacag ctcctgatga gctcgcagaa     480
aaagcagagc aatcacattt gttgacccta aagattatt tttcttatat aatatacacc      540
acatcatgta aataaaaatt tcaaattcta tgttgacaat gaatttgaat tactgttaag     600
attaccaaca aatgattcaa cttttcaaaa aattaataac attttctctt atcgagagtt     660
gggcgaggga ttggccttt gaccccaaca gcaaccgacc gtaataccat tgtgaaatgg      720
ggcgcactgc ttttcgcgcc gagactgatg tctcataagg cacggtgcta attccatcag     780
attgtgtctg agagatgaga gaggcagtgt tttacgtaga aaagcctctt tctctcatgg     840
gaaagaggct ttttgttgtg agaaaacctc ttagcagcct gtatccgcgg gtgaaagaga     900
gtgttttaca tataaaggag gagaaacaat gacaaccatc aaaacatcga atttaggatt     960
tccgagaatc gacctgaaaa tgtcgtccag tgcgatggaa ttctgatcaa atggttcagt    1020
gagagcgaag cgaacacttg attttttaat tttctatctt ttataggtca ttagagtata    1080
cttatttgtc ctataaacta tttagcagca taatagattt attgaatagg tcatttaagt    1140
tgagcatatt agaggaggaa atcttggag aaatatttga agaacccgaa cgcgtgagta     1200
gttcaacaaa cgggccagtt tgttgaagat tagatgctat aattgttatt aaaaggattg    1260
aaggatgctt aggaagacga gttattaata gctgaataag aacggtgctc tccaaatatt    1320
cttatttaga aaagcaaatc taaaattatc tgaaaaggga atgagaatag tgaatggacc    1380
aataataatg actagagaag aaagaatgaa gattgttcat gaaattaagg aacgaatatt    1440
ggataaatat ggggatgatg ttaaggctat tggtgtttat ggctctcttg gtcgtcagac    1500
tgatgggccc tattcggata ttgagatgat gtgtgtcatg tcaacagagg aagcagagtt    1560
cagccatgaa tggacaaccg gtgagtggaa ggtggaagtg aattttgata gcgaagagat    1620
tctactagat tatgcatctc aggtggaatc agattggccg cttacacatg gtcaattttt    1680
ctctattttg ccgatttatg attcaggtgg atacttagaa aaagtgtatc aaactgctaa    1740
atcggtagaa gcccaaacgt tccacgatgc gatttgtgcc cttatcgtag aagagctgtt    1800
tgaatatgca ggcaaatggc gtaatattcg tgtgcaagga ccgacaacat ttctaccatc    1860
cttgactgta caggtagcaa tggcaggtgc catgttgatt ggtctgcatc atcgcatctg    1920
ttatacgacg agcgcttcgg tcttaactga agcagttaag caatcagatc ttccttcagg    1980
ttatgaccat ctgtgccagt tcgtaatgtc tggtcaactt tccgactctg agaaacttct    2040
ggaatcgcta gagaatttct ggaatgggat tcaggagtgg acagaacgac acggatatat    2100
agtggatgtg tcaaaacgca taccattttg aacgatgacc tctaataatt gttaatcatg    2160
ttggagctca gtgagagcga agcgaacact tgatttttta attttctatc ttttataggt    2220
```

```
cattagagta tacttatttg tcctataaac tatttagcag cataatagat ttattgaata    2280
ggtcatttaa gttgagcata ttagaggagg aaaatcttgg agaaatattt gaagaacccg    2340
aggcctttca ggcccgcaaa caatatggtt gaagccgcaa acaggcaag  agcacagcag    2400
acacagctag tataatttga aaaaaccatc tgcatttggc agatggtttt tttctataat    2460
acagccacaa tcggtttctt atttagcaaa tcccccaaat actttgttta ttttgcactt    2520
ttttaagaat gttctttgca ttcttttcgg ctatactaat aacactctat tgacaggagg    2580
gattgggatg aatcatgaaa cgttcttaaa acgggctgtc actctcgcat gtgaaggagt    2640
gaatgcagga atcggcgggc cttttggagc cgttatcgtg aaagacggag ccattattgc    2700
agagggacag aacaacgtca caacaagcaa tgatccgact gcccacgcgg aagtcacagc    2760
tattcggaaa gcctgtaagg tgctaggagc ctaccagctt gatgactgca ttttgtatac    2820
gagctgtgaa ccatgcccaa tgtgcttggg cgccatctac tgggcccggc taaagccgt    2880
tttctatgca gctgagcaca cagacgctgc cgaagccggg tttgatgatt cattcattta    2940
taaagaaatt gataaacctg ctgaagaaag aacgatcccc tttatcaag  tgacactaac    3000
agagcattta tccccgtttc aagcatggcg gaacttcgcc aataagaaag aatattaaaa    3060
ggatcaggca tgcgcggcct ggtccttgtt atttctccaa gtagccgcta tgccctgtgc    3120
aaatacaaaa cagcatatac gcgcaattca gcacggcaga caccgtgcca gccacccgct    3180
tcatctgtaa cttttggttt aaaggcatgc ttcaaacgct tctctgaagt tttatcataa    3240
atctgtgccc gccccgcatg tccgacacca aaaacatcc  tgagaatcct caggatgccg    3300
gtcattattt taattctagt tttacatcaa catttcctct ggttgccttt gagtaaggac    3360
agaattcatg agcggcgttg acaagctctt gtgccttttc ccgatctaaa tctttcgtgt    3420
tcacaacaag tgtgacaccg attttaaacc cgccgtcgct ctcatccttc atgaggctga    3480
cctgcccttc aatctccgaa tcaatttcga tattctgctc tttggctacg tgttcgagcg    3540
cgccgccgaa gcatgcagca taccctgccg caaagagctg ttccggattt gtgccggttt    3600
gtccttcttt tttggcattt ggcatgacaa tatcaaaatc aagaacaccg tcatctgatg    3660
taatatgtcc tgctcgtccg cctcgcgcgg ttacttttgc tgtaaatagt gccatatttc    3720
ccaacctcct tatttgtatc tagttgttat atttcccttt ctgatctttt taaacatgct    3780
atgtttgccg agaataggaa aagtgaggtt tttcagatac aatagaatcg aatgacaaaa    3840
aagagttggt gaacaaaatg gaaaataaat ttgatcatat gcggtgtgaa ataccgcaca    3900
gatgcgtaag gagaaaatac cgcatcaggc gctcttccgc ttcctcgctc actgactcgc    3960
tgcgctcggt cgttcggctg cggcgagcgg tatcagctca ctcaaaggcg gtaatacggt    4020
tatccacaga atcaggggat aacgcaggaa agaacatgtg agcaaaaggc cagcaaaagg    4080
ccaggaaccg taaaaaggcc gcgttgctgg cgttttttcca taggctccgc cccctgacg   4140
agcatcacaa aaatcgacgc tcaagtcaga ggtggcgaaa cccgacagga ctataaagat    4200
accaggcgtt tcccctgga  agctccctcg tgcgctctcc tgttccgacc ctgccgctta    4260
ccggatacct gtccgccttt ctcccttcgg gaagcgtggc gctttctcat agctcacgct    4320
gtaggtatct cagttcggtg taggtcgttc gctccaagct gggctgtgtg cacgaacccc    4380
ccgttcagcc cgaccgctgc gccttatccg gtaactatcg tcttgagtcc aacccggtaa    4440
gacacgactt atcgccactg gcagcagcca ctggtaacag gattagcaga gcgaggtatg    4500
taggcggtgc tacagagttc ttgaagtggt ggcctaacta cggctacact agaaggacag    4560
tatttggtat ctgcgctctg ctgaagccag ttaccttcgg aaaaagagtt ggtagctctt    4620
```

```
gatccggcaa acaaaccacc gctggtagcg gtggttttt tgtttgcaag cagcagatta    4680
cgcgcagaaa aaaggatct caagaagatc ctttgatctt ttctacgggg tctgacgctc    4740
agtggaacga aaactcacgt taagggattt tggtcatgag attatcaaaa aggatcttca    4800
cctagatcct tttaaattaa aaatgaagtt ttaaatcaat ctaaagtata tatgagtaaa    4860
cttggtctga cagttaccaa tgcttaatca gtgaggcacc tatctcagcg atctgtctat    4920
ttcgttcatc catagttgcc tgactccccg tcgtgtagat aactacgata cgggagggct    4980
taccatctgg ccccagtgct gcaatgatac cgcgagaccc acgctcaccg gctccagatt    5040
tatcagcaat aaaccagcca gccggaaggg ccgagcgcag aagtggtcct gcaactttat    5100
ccgcctccat ccagtctatt aattgttgcc gggaagctag agtaagtagt tcgccagtta    5160
atagtttgcg caacgttgtt gccattgctg caggcatcgt ggtgtcacgc tcgtcgtttg    5220
gtatggcttc attcagctcc ggttcccaac gatcaaggcg agttacatga tcccccatgt    5280
tgtgcaaaaa agcggttagc tccttcggtc tccgatcgt tgtcagaagt aagttggccg    5340
cagtgttatc actcatggtt atggcagcac tgcataattc tcttactgtc atgccatccg    5400
taagatgctt ttctgtgact ggtgagtact caaccaagtc attctgagaa tagtgtatgc    5460
ggcgaccgag ttgctcttgc ccggcgtcaa cacgggataa taccgcgcca catagcagaa    5520
ctttaaaagt gctcatcatt ggaaaacgtt cttcggggcg aaaactctca aggatcttac    5580
cgctgttgag atccagttcg atgtaaccca ctcgtgcacc caactgatct tcagcatctt    5640
ttactttcac cagcgtttct gggtgagcaa aaacaggaag gcaaaatgcc gcaaaaaagg    5700
gaataagggc gacacggaaa tgttgaatac tcatactctt cctttttcaa tattattgaa    5760
gcatttatca gggttattgt ctcatgagcg gatacatatt tgaatgtatt tagaaaaata    5820
aacaaatagg ggttccgcgc acatttcccc gaaaagtgcc acctgacgtc taagaaacca    5880
ttattatcat gacattaacc tataaaaata ggcgtatcac gaggcccttt cgtcttcaag    5940
aattctcatg tttgacagct tatcatcgat aagctttaat gcggtagttt atcacagtta    6000
aattgctaac gcagtcaggc accgtgtatg aaatctaaca atgcgctcat cgtcatcctc    6060
ggcaccgtca ccctggatgc tgtaggcata ggcttggtta tgccggtact gccgggcctc    6120
ttgcgggata tcgtccattc cgacagcatc gccagtcact atggcgtgct gctagcgcta    6180
tatgcgttga tgcaatttct atgcgcaccc gttctcggag cactgtccga ccgctttggc    6240
cgccgcccag tcctgctcgc ttcgctactt ggagccacta tcgactacgc gatcatggcg    6300
accacacccg tcctgtggat cctctacgcc ggacgcatcg tggccggcat caccggcgcc    6360
acaggtgcgg ttgctggcgc ctatatcgcc gacatcaccg atggggaaga tcgggctcgc    6420
cacttcgggc tcatgagcgc ttgtttcggc gtgggtatgg tggcaggccc cgtggccggg    6480
ggactgttgg gcgccatctc cttgcatgca ccattccttg cggcggcggt gctcaacggc    6540
ctcaacctac tactgggctg cttcctaatg caggagtcgc ataagggaga gcgtcgaccg    6600
atgcccttga gagccttcaa cccagtcagc tccttccggt gggcgcgggg catgactatc    6660
gtcgccgcac ttatgactgt cttctttatc atgcaactcg taggacaggt gccggcagcg    6720
ctctgggtca ttttcggcga ggaccgcttt cgctggagcg cgacgatgat cggcctgtcg    6780
cttgcggtat tcggaatctt gcacgccctc gctcaagcct tcgtcactgg tcccgccacc    6840
aaacgtttcg gcgagaagca ggccattatc gccggcatgg cggccgacgc gctgggctac    6900
gtcttgctgg cgttcgcgac gcgaggctgg atggccttcc ccattatgat tcttctcgct    6960
```

```
tccggcggca tcgggatgcc cgcgttgcag gccatgctgt ccaggcaggt agatgacgac      7020
catcagggac agcttcaagg atcgctcgcg gctcttacca gcctaacttc gatcactgga      7080
ccgctgatcg tcacggcgat ttatgccgcc tcggcgagca catggaacgg gttggcatgg      7140
attgtaggcg ccgccctata ccttgtctgc ctccccgcgt tgcgtcgcgg tgcatggagc      7200
cgggccacct cgacctgaat ggaagccggc ggcacctcgc taacggattc accactccaa      7260
gaattggagc caatcaattc ttgcggagaa ctgtgaatgc gcaaaccaac c               7311
```

<210> SEQ ID NO 8
<211> LENGTH: 13129
<212> TYPE: DNA
<213> ORGANISM: artificial sequence
<220> FEATURE:
<223> OTHER INFORMATION: Synthetic construct
<220> FEATURE:
<221> NAME/KEY: misc_feature
<222> LOCATION: (5067)..(5067)
<223> OTHER INFORMATION: n is a, c, g, or t

<400> SEQUENCE: 8

```
aacaaaattc tccagtcttc acatcggttt gaaaggagga agcggaagaa tgaagtaaga        60 gggattttg actccgaagt aagtcttcaa aaaatcaaat aaggagtgtc aagaatgttt        120
gcaaaacgat tcaaaacctc tttactgccg ttattcgctg attttttatt gctgtttcat       180
ttggttctgg caggaccggc ggctgcgagt gctgaaacgg cgaacaaatc gaatgagctt       240
acagcaccgt cgatcaaaag cggaaccatt cttcatgcat ggaattggtc gttcaatacg       300
ttaaaacaca atatgaagga tattcatgat gcaggatata cagccattca gacatctccg       360
attaaccaag taaggaagg gaatcaagga gataaaagca tgtcgaactg gtactggctg        420
tatcagccga catcgtatca aattggcaac cgttacttag gtactgaaca agaatttaaa       480
gaaatgtgtg cagccgctga agaatatggc ataaaggtca ttgttgacgc gcggccgcgg       540
atctaaatta tactagctgt gtctgctgtg ctcttgcctg ttttgcggct tcaaccatat       600
ttttcaatgc tgcaaccgtt tcttcctgct gtcttgtttt caatccgcag tctggattta       660
cccagaagcg gtcagtcgga cagacggcaa gcgcatcaac gataatattg tacatttctt       720
cagttgacgg cacacgaggg ctgtgaatgt catatacacc aaggccaagc cctttcaaat       780
acgggtggtt tttaagtaa tctaaaaatc ctccgtggct tctgctatgt tcgattgtaa       840
tcacatcggc atcaagatca ttgattgtat caacgatatc ttcgaagttg ctgtagcaca       900
tatgtgtatg aatttgtgtc tcgttttca cggaagaagt ggttaatctg aaagcttctg        960
ccgcccaagt caaatactca tcccaatcgc gggttttcaa tggaaggcct tcacgcagcg      1020
ctggttcatc gacttgaatg atttgaatgc ctgcgtcttc aagcgcttta acttctttgc      1080
gaagggcaag cccgatttgg aaggcgattt ctttcctcga gatgtcgttt cgagggaaag      1140
accagtttaa gattgtaacc gggccgtca gcattccttt cacatgcttg gaagtcaatg       1200
actgtgcgta gactgtgtct ttcactgtca tcggttcaat aaattcaaca tctccgtaaa      1260
tgactggcgg gcggacacag cgtgagccgt atgattgaac ccaggcatat ttagtgaagg      1320
cgaaaccggc cagcttttca ccgaagtatt cgaccatgtc tgtccgttca aattcgccgt      1380
gaacaaggac atcaagctcc aattcttcct gaatatcaat ccatcttttt gtttccgcat      1440
tgataaagtt ttgatactgt tcatcggacc actcagcttt ccgccatttt ggcgtgccc       1500 tccgcacttc agcagactgc gggaagctgc cgatcgttgt cgtcggcaaa agcggaaggc      1560
cgagagattc attttgtagg gctaaacgtt cttcaaacgg aatcgggcgc ttgaagtctt      1620
```

```
tatcagttaa ttgctcaagc tctttctttt gttcagaatt ggcgcctgtt gcaaactgtt    1680
taagcgcctg gatatcagcc ttagcctgct gaatctcttc gctgatcgcc gcttttcctg    1740
atactaagcc ttctttcaaa gctgtcagct cggccagctt ttcttttgcg taggataatc    1800
cgttcaatag gtctttttcc aaatgctcat cagggtgttt cgctactgga acatcgagca    1860
ggctgctgga aggctgaatc cacagttcat caacttttgc aatgctgaga acatcaagaa    1920
cggcatcgag actctcttca aggtccgctt tccaaatgtt gcgtccgtcg ataacgccgg    1980
ctgccagcac tttatctgtc gggaagccat gtgttttaag ctgttccagg tttctgcctt    2040
tgtcgtgaac gaaatcaagg ccaattccct gaaccgggta agagatcagc tcttcataag    2100
catcaacaga atcaaaatac gtctgcaaaa gcacattcaa ggatgaaagc tcacttgtaa    2160
tgctttcaaa taattctttt gcgccgcgta catcttcact agaggcggta acgagcgccg    2220
gctcatcgat ttgaacccat tttacgcctt cttcttcaag ctctttcaaa agctgtacat    2280
ataatggcac aaggcgtttt tggatcgctt ttgcttcaga cggttcatag cctttagcaa    2340
gcgtaacgaa cgtataaggg ccgacaatca caggctttgt ttccacaccg tattcctgtt    2400
tgatccggcg ataatcttcg agttgtttgt ttcttgtcag acggaactca atgctctcgt    2460
catattccgg aacgatgtaa tggtaatttg tattaaacca ttttgtcatt tcactagata    2520
cagcgtcttt gattccgcgg gcgatagcga agtatgtatc ggtagcgtca gtcaaatgtc    2580
tgaaccgttt cgggatccag ttgaagctga ctgctgtgtc gagtacatgg tcatactgtg    2640
tgaaatcaga acaggcaca acatcaatct gctggtcaat ttgtgttttt actgcggata    2700
aaaatagttc gtcgatttgc ttcaaaaacg tatctttatc agtactgcct ttccaatacg    2760
cttcaagtgc ttttttccat tcccggttca ggtcgattct cggaaatcct aaattcgatg    2820
ttttgatggt tgtcattgtt tctcctccag atccgtcgac ctgcataaac tgcatccctt    2880
aacttgtttt atttgtatag ttcatccatg ccatgtgtaa tcccagcagc tgttacaaac    2940
tcaagaagga tcatgtgatc tctcttttcg ttgggatctt tggaaagggc agattgcgtg    3000
gacaggtaat ggttgtctgg taaaaggaca gggccatcgc caattggagt attttgttga    3060
taatggtctg ctaattgaac gcttccatct ttaatgttgt gtctaatttt gaagttaact    3120
ttgatgccat tctttggttt gtctgccatg atgtatacat tatgtgagtt ataattgtat    3180 tccatttttgt gtccaagaat gttttccatct tctttaaaat caataccttt taactcgatt    3240
ctattaacaa gggtatcacc ttcaaacttg acttcagcac gtgtcttgta gttcccgtca    3300
tctttgtaaa atatagttct ttcctgtaca taaccttcgg gcatggcact cttgaaaaag    3360
tcatgctgtt tcatatgatc tgggtatcta gaaaagcatt gaacaccata agagagagta    3420
gtgacaagcg ttggccatgg aacaggtagc ttcccagtag tgcaaataaa tttaagggta    3480
agttttccgt atgttgcatc accttcaccc tctccactaa cagagaattt tgcccatta    3540 acatcgccat ctaattcaac aagaattggg acaactccag tgaaaagttc ttctccttta    3600
ctcataaagc ttccctccta gcttttattc aatatcattt acatatcata ctaaaattaa    3660
aggctaaagg gaaacgatgt ctaacgaaaa aaaggccaaa tcatgtttgg cctttggcgg    3720
ttatttcgat gattgtcccg aattctggcc cttaaggcca attctcatgt tgacagctt    3780 atcatcggca atagttaccc ttattatcaa gataagaaag aaaaggattt ttcgctacgc    3840
tcaaatcctt taaaaaaaca caaaagacca catttttaa tgtggtcttt attcttcaac    3900
taaagcaccc attagttcaa caaacgaaaa ttggataaag tgggatattt ttaaaatata    3960
```

```
tatttatgtt acagtaatat tgactttttaa aaaaggattg attctaatga agaaagcaga    4020
caagtaagcc tcctaaattc actttagata aaaatttagg aggcatatca aatgaacttt    4080
aataaaattg atttagacaa ttggaagaga aaagagatat ttaatcatta tttgaaccaa    4140
caaacgactt ttagtataac cacagaaatt gatattagtg ttttataccg aaacataaaa    4200
caagaaggat ataaatttta ccctgcattt attttcttag tgacaagggt gataaactca    4260 aatcagctt ttagaactgg ttacaatagc gacggagagt taggttattg ggataagtta    4320
gagccacttt atacaatttt tgatggtgta tctaaaacat tctctggtat ttggactcct    4380
gtaaagaatg acttcaaaga gttttatgat ttataccttt ctgatgtaga gaaatataat    4440
ggttcgggga aattgtttcc caaaacacct atacctgaaa atgcttttc tctttctatt    4500 attccatgga cttcatttac tgggtttaac ttaaatatca ataataatag taattacctt    4560
ctacccatta ttacagcagg aaaattcatt aataaaggta attcaatata tttaccgcta    4620
tctttacagg tacatcattc tgtttgtgat ggttatcatg caggattgtt tatgaactct    4680
attcaggaat tgtcagatag gcctaatgac tggcttttat aatatgagat aatgccgact    4740
gtacttttta cagtcggttt tctaatgtca ctaacctgcc ccgttagttg aagaaggttt    4800
ttatattaca gctccagatc ctctacgccg acgcatcgt ggccggcatc accgcgcca    4860 caggtgcggt tgctggcgcc tatatcgccg acatcaccga tggggaagat cgggctcgcc    4920
acttcgggct catgagcgct tgtttcggcg tgggtatggt ggcaggcccc gtggccgggg    4980
gactgttggg cgccatctcc ttgcatgccc agaaatttat ccttaagctg gattcaggaa    5040
gaggggcgtt tgacaggaag ggggagnagg catataatga gatgagtact gttaactggg    5100
caggatggat ccccagcttg ttgatacact aatgctttta tatagggaaa aggtggtgaa    5160
ctactgtgga agttactgac gtaagattac gggtcgaccg ggaaaaccct ggcgttaccc    5220
aacttaatcg ccttgcagca catccccctt tcgccagctg gcgtaatagc gaagaggccc    5280
gcaccgatcg cccttcccaa cagttgcgca gcctgaatgg cgaatggcgc tttgcctggt    5340
ttccggcacc agaagcggtg ccggaaagct ggctggagtg cgatcttcct gaggccgata    5400
ctgtcgtcgt cccctcaaac tggcagatgc acggttacga tgcgcccatc tacaccaacg    5460
taacctatcc cattacggtc aatccgccgt ttgttcccac ggagaatccg acgggttgtt    5520
actcgctcac atttaatgtt gatgaaagct ggctacagga aggccagacg cgaattattt    5580
ttgatggcgt taactcggcg tttcatctgt ggtgcaacgg gcgctgggtc ggttacggcc    5640
aggacagtcg tttgccgtct gaatttgacc tgagcgcatt tttacgcgcc ggagaaaacc    5700
gcctcgcggt gatggtgctg cgctggagtg acggcagtta tctggaagat caggatatgt    5760
ggcggatgag cggcattttc cgtgacgtct cgttgctgca taaaccgact acacaaatca    5820
gcgatttcca tgttgccact cgctttaatg atgatttcag ccgcgctgta ctggaggctg    5880
aagttcagat gtgcggcgag ttgcgtgact acctacgggt aacagtttct ttatggcagg    5940
gtgaaacgca ggtcgccagc ggcaccgcgc ctttcggcgg tgaaattatc gatgagcgtg    6000
gtggttatgc cgatcgcgtc acactacgtc tgaacgtcga aaacccgaaa ctgtggagcg    6060
ccgaaatccc gaatctctat cgtgcggtgg ttgaactgca caccgccgac ggcacgctga    6120
ttgaagcaga agcctgcgat gtcggttttc gcgaggtgcg gattgaaaat ggtctgctgc    6180
tgctgaacgg caagccgttg ctgattgagg cgttaaccg tcacgagcat catcctctgc    6240
atggtcaggt catggatgag cagacgatgg tgcaggatat cctgctgatg aagcagaaca    6300
actttaacgc cgtgcgctgt tcgcattatc cgaaccatcc gctgtggtac acgctgtgcg    6360
```

```
accgctacgg cctgtatgtg gtggatgaag ccaatattga aacccacggc atggtgccaa    6420
tgaatcgtct gaccgatgat ccgcgctggc taccggcgat gagcgaacgc gtaacgcgaa    6480
tggtgcagcg cgatcgtaat cacccgagtg tgatcatctg gtcgctgggg aatgaatcag    6540
gccacggcgc taatcacgac gcgctgtatc gctggatcaa atctgtcgat ccttcccgcc    6600
cggtgcagta tgaaggcggc ggagccgaca ccacggccac cgatattatt tgcccgatgt    6660
acgcgcgcgt ggatgaagac cagcccttcc cggctgtgcc gaaatggtcc atcaaaaaat    6720
ggctttcgct acctggagag acgcgcccgc tgatcctttg cgaatacgcc cacgcgatgg    6780
gtaacagtct tggcggtttc gctaaatact ggcaggcgtt tcgtcagtat ccccgtttac    6840
agggcggctt cgtctgggac tgggtggatc agtcgctgat taaatatgat gaaaacggca    6900
acccgtggtc ggcttacggc ggtgattttg gcgatacgcc gaacgatcgc cagttctgta    6960
tgaacggtct ggtctttgcc gaccgcacgc cgcatccagc gctgacggaa gcaaaacacc    7020
agcagcagtt tttccagttc cgtttatccg ggcaaaccat cgaagtgacc agcgaatacc    7080
tgttccgtca tagcgataac gagctcctgc actggatggt ggcgctggat ggtaagccgc    7140
tggcaagcgg tgaagtgcct ctggatgtcg ctccacaagg taaacagttg attgaactgc    7200
ctgaactacc gcagccggag agcgccgggc aactctggct cacagtacgc gtagtgcaac    7260
cgaacgcgac cgcatggtca gaagccgggc acatcagcgc ctggcagcag tggcgtctgg    7320
cggaaaacct cagtgtgacg ctccccgccg cgtcccacgc catcccgcat ctgaccacca    7380
gcgaaatgga ttttgcatc gagctgggta ataagcgttg gcaatttaac cgccagtcag    7440
gctttctttc acagatgtgg attggcgata aaaacaact gctgacgccg ctgcgcgatc    7500
agttcacccg tgcaccgctg gataacgaca ttggcgtaag tgaagcgacc cgcattgacc    7560
ctaacgcctg ggtcgaacgc tggaaggcgg cgggccatta ccaggccgaa gcagcgttgt    7620
tgcagtgcac ggcagataca cttgctgatg cggtgctgat tacgaccgct cacgcgtggc    7680
agcatcaggg gaaaacctta tttatcagcc ggaaaaccta ccggattgat ggtagtggtc    7740
aaatggcgat taccgttgat gttgaagtgg cgagcgatac accgcatccg gcgcggattg    7800
gcctgaactg ccagctggcg caggtagcag agcgggtaaa ctggctcgga ttagggccgc    7860
aagaaaacta tcccgaccgc cttactgccg cctgttttga ccgctgggat ctgccattgt    7920
cagacatgta taccccgtac gtcttcccga gcgaaaacgg tctgcgctgc gggacgcgcg    7980
aattgaatta tggcccacac cagtggcgcg cgacttcca gttcaacatc agccgctaca    8040
gtcaacagca actgatggaa accagccatc gccatctgct gcacgcggaa gaaggcacat    8100
ggctgaatat cgacggtttc catatgggga ttggtggcga cgactcctgg agcccgtcag    8160
tatcggcgga attacagctg agcgccgtc gctaccatta ccagttggtc tggtgtcaaa    8220
aataagcatg caccattcct tgcggcggcg gtgctcaacg gcctcaacct actactgggc    8280
tgcttcctaa tgcaggagtc gcataaggga gagcgtcgac atggatgagc gatgatgata    8340
tccgtttagg ctgggcggtg atagcttctc gttcaggcag tacgcctctt ttcttttcca    8400
gacctgaggg aggcggaaat ggtgtgaggt tcccggggaa aagccaaata ggcgatcgcg    8460
ggagtgcttt atttgaagat caggctatca ctgcggtcaa tagatttcac aatgtgatgg    8520
ctggacagcc tgaggaactc tcgaacccga atggaaacaa ccagatattt atgaatcagc    8580
gcggctcaca tggcgttgtg ctggcaaatg caggttcatc ctctgtctct atcaatacgg    8640
caacaaaatt gcctgatggc aggtatgaca ataaagctgg agcgggttca tttcaagtga    8700
```

```
acgatggtaa actgacaggc acgatcaatg ccaggtctgt agctgtgctt tatcctgatg      8760
atattgcaaa agcgcctcat gttttccttg agaattacaa aacaggtgta acacattctt      8820
tcaatgatca actgacgatt accttgcgtg cagatgcgaa tacaacaaaa gccgtttatc      8880
aaatcaataa tggaccagac gacaggcgtt taaggatgga gatcaattca caatcggaaa      8940
aggagatcca atttggcaaa acatacacca tcatgttaaa aggaacgaac agtgatggtg      9000
taacgaggac cgagaaatac agttttgtta aaagagatcc agcgtcggcc aaaaccatcg      9060
gctatcaaaa tccgaatcat tggagccagg taaatgctta tatctataaa catgatggga      9120
gccgagtaat tgaattgacc ggatcttggc ctggaaaacc aatgactaaa aatgcagacg      9180
gaatttacac gctgacgctg cctgcggaca cggatacaac caacgcaaaa gtgattttta      9240
ataatggcag cgcccaagtg cccggtcaga atcagcctgg cttttgattac gtgctaaatg      9300 gtttatataa tgactcgggc ttaagcggtt ctcttcccca ttgagggcaa ggctagacgg      9360
gacttaccga agaaaccat caatgatggt ttctttttg ttcataaatc agacaaaact      9420
tttctcttgc aaaagtttgt gaagtgttgc acaatataaa tgtgaaatac ttcacaaaca      9480
aaaagacatc aaagagaaac ataccctgca aggatgctga tattgtctgc atttgcgccg      9540
gagcaaacca aaaacctggt gagacacgcc ttgaattagt agaaaagaac ttgaagattt      9600
tcaaaggcat cgttagtgaa gtcatggcga gcggatttga cggcattttc ttagtcggta      9660
acaatcctcg ttaaaggaca aggacctgag cggaagtgta tcgtacagta gacggagtat      9720
actagtatag tctatagtcc gtggaattat tatatttatc tccgacgata ttctcatcag      9780
tgaaatccag ctggagttct ttagcaaatt tttttattag ctgaacttag tattagtggg      9840
gccgctgata attactaata ctaggagaag ttaataaata cgtaaccaac atgattaaca      9900
attattagag gtcatcgttc aaaatggtat gcgttttgac acatccacta tatatccgtg      9960
tcgttctgtc cactcctgaa tcccattcca gaaattctct agcgattcca gaagtttctc     10020
agagtcggaa agttgaccag acattacgaa ctggcacaga tggtcataac ctgaaggaag     10080
atctgattgc ttaactgctt cagttaagac cgaagcgctc gtcgtataac agatgcgatg     10140
atgcagacca atcaacatgg cacctgccat tgctacctgt acagtcaagg atggtagaaa     10200
tgttgtcggt ccttgcacac gaatattacg ccatttgcct gcatattcaa acagctcttc     10260
tacgataagg gcacaaatcg catcgtggaa cgtttgggct tctaccgatt tagcagtttg     10320
atacactttc tctaagtatc cacctgaatc ataaatcggc aaaatagaga aaaattgacc     10380
atgtgtaagc ggccaatctg attccacctg agatgcataa tctagtagaa tctcttcgct     10440
atcaaaattc acttccacct tccactcacc ggttgtccat tcatggctga actctgcttc     10500
ctctgttgac atgacacaca tcatctcaat atccgaatag ggcccatcag tctgacgacc     10560
aagagagcca taaacaccaa tagccttaac atcatcccca tatttatcca atattcgttc     10620
cttaatttca tgaacaatct tcattctttc ttctctagtc attattattg gtccattcac     10680
tattctcatt cccttttcag ataatttag atttgctttt ctaaataaga atatttggag     10740
agcaccgttc ttattcagct attaataact cgtcttccta agcatcatgg tctcactttt     10800 ccacttttg tcttgtccac taaaacccctt gattttcat ctgaataaat gctactatta     10860
ggacacataa tattaaaaga aaccccatc tatttagtta tttgtttagt cacttataac     10920
tttaacagat ggggttttc tgtgcaacca attttaaggg ttttcaatac tttaaaacac     10980
atacatacca acacttcaac gcacctttca gcaactaaaa taaaaatgac gttatttcta     11040
tatgtatcaa gataagaaag aacaagttca aaaccatcaa aaaaagacac cttttcaggt     11100
```

```
gcttttttta ttttataaac tcattccctg atctccccat actcctccaa tccaaagcta    11160
tttagaaaga ttactatatc ctcaaacagg cggtaaccgg cctcttcatc gggaatgcgc    11220
gcgaccttca gcatcgccgg catgtccccc tggcggacgg gaagtatcca gctcgaggtc    11280
gggccgcgtt gctggcgttt ttccataggc tccgccccc tgacgagcat cacaaaaatc     11340
gacgctcaag tcagaggtgg cgaaacccga caggactata agataccag gcgtttcccc     11400 ctggaagctc cctcgtgcgc tctcctgttc cgacctgcc gcttaccgga tacctgtccg     11460
cctttctccc ttcgggaagc gtggcgcttt ctcatagctc acgctgtagg tatctcagtt    11520
cggtgtaggt cgttcgctcc aagctgggct gtgtgcacga accccccgtt cagcccgacc    11580
gctgcgcctt atccggtaac tatcgtcttg agtccaaccc ggtaagacac gacttatcgc    11640
cactggcagc agccactggt aacaggatta gcagagcgag gtatgtaggc ggtgctacag    11700
agttcttgaa gtggtggcct aactacggct acactagaag gacagtattt ggtatctgcg    11760
ctctgctgaa gccagttacc ttcggaaaaa gagttggtag ctcttgatcc ggcaaacaaa    11820
ccaccgctgg tagcggtggt ttttttgttt gcaagcagca gattacgcgc agaaaaaaag    11880
gatctcaaga agatcctttg atcttttcta cggggtctga cgctcagtgg aacgaaaact    11940
cacgttaagg gattttggtc atgagattat caaaaaggat cttcacctag atccttttaa    12000
attaaaaatg aagttttaaa tcaatctaaa gtatatatga gtaaacttgg tctgacagtt    12060
accaatgctt aatcagtgag gcacctatct cagcgatctg tctatttcgt tcatccatag    12120
ttgcctgact ccccgtcgtg tagataacta cgatacggga gggcttacca tctggcccca    12180
gtgctgcaat gataccgcga gacccacgct caccggctcc agatttatca gcaataaacc    12240
agccagccgg aagggccgag cgcagaagtg gtcctgcaac tttatccgcc tccatccagt    12300
ctattaattg ttgccgggaa gctagagtaa gtagttcgcc agttaatagt ttgcgcaacg    12360
ttgttgccat tgctgcaggc atcgtggtgt cacgctcgtc gtttggtatg gcttcattca    12420
gctccggttc ccaacgatca aggcgagtta catgatcccc catgttgtgc aaaaaagcgg    12480
ttagctcctt cggtcctccg atcgttgtca gaagtaagtt ggccgcagtg ttatcactca    12540
tggttatggc agcactgcat aattctctta ctgtcatgcc atccgtaaga tgcttttctg    12600
tgactggtga gtactcaacc aagtcattct gagaatagtg tatgcggcga ccgagttgct    12660
cttgcccggc gtcaacacgg gataataccg cgccacatag cagaacttta aaagtgctca    12720
tcattggaaa acgttcttcg gggcgaaaac tctcaaggat cttaccgctg ttgagatcca    12780
gttcgatgta acccactcgt gcacccaact gatcttcagc atcttttact ttcaccagcg    12840
tttctgggtg agcaaaaaca ggaaggcaaa atgccgcaaa aaagggaata agggcgacac    12900
ggaaatgttg aatactcata ctcttccttt ttcaatatta ttgaagcatt tatcagggtt    12960
attgtctcat gagcggatac atatttgaat gtatttagaa aaataaacaa ataggggttc    13020
cgcgcacatt tccccgaaaa gtgccacctg acgtctaaga aaccattatt atcatgacat    13080
taacctataa aaataggcgt atcacgaggc cctttcgtct tcaagaatt                13129
```

\<210\> SEQ ID NO 9
\<211\> LENGTH: 87
\<212\> TYPE: DNA
\<213\> ORGANISM: artificial sequence
\<220\> FEATURE:
\<223\> OTHER INFORMATION: Synthetic construct

```
<400> SEQUENCE: 9
gaattcatgc atcgcggagg tgagatttga cactagtagg ctacgggact ataatgcggg      60
aagtactgtt aactgcagga taagctt                                         87

<210> SEQ ID NO 10
<211> LENGTH: 86
<212> TYPE: DNA
<213> ORGANISM: artificial sequence
<220> FEATURE:
<223> OTHER INFORMATION: Synthetic construct

<400> SEQUENCE: 10
gaattcatgc attcgaattt ggaaatcgac aggagcgggc gggtagggta taatatatgt      60
agtactgtta actgcaggat aagctt                                          86

<210> SEQ ID NO 11
<211> LENGTH: 87
<212> TYPE: DNA
<213> ORGANISM: artificial sequence
<220> FEATURE:
<223> OTHER INFORMATION: Synthetic construct

<400> SEQUENCE: 11
gaattcatgc atcgagcgga agtttgttga cacagctcca ggatacaaat ataatgggtc      60
gagtactgtt aactgcagga taagctt                                         87

<210> SEQ ID NO 12
<211> LENGTH: 86
<212> TYPE: DNA
<213> ORGANISM: artificial sequence
<220> FEATURE:
<223> OTHER INFORMATION: Synthetic construct

<400> SEQUENCE: 12
gaattcatgc atggacagtt cgtctttgac aaatctaaga aagggaacta taatgtgggc      60
agtactgtta actgcaggat aagctt                                          86

<210> SEQ ID NO 13
<211> LENGTH: 87
<212> TYPE: DNA
<213> ORGANISM: artificial sequence
<220> FEATURE:
<223> OTHER INFORMATION: Synthetic construct

<400> SEQUENCE: 13
gaattcatgc atgcggatgg aaggggttga caccggcgcc gggtccaggt ataatcttga      60
cagtactgtt aactgcagga taagctt                                         87

<210> SEQ ID NO 14
<211> LENGTH: 87
<212> TYPE: DNA
<213> ORGANISM: artificial sequence
<220> FEATURE:
<223> OTHER INFORMATION: Synthetic construct

<400> SEQUENCE: 14
gaattcatgc atagaggagt ttattcttga caaatgcgag gcagaatggt ataatacgta      60
gagtactgtt aactgcagga taagctt                                         87
```

<210> SEQ ID NO 15
<211> LENGTH: 87
<212> TYPE: DNA
<213> ORGANISM: artificial sequence
<220> FEATURE:
<223> OTHER INFORMATION: Synthetic construct

<400> SEQUENCE: 15

```
gaattcatgc atagtaaagt ttattcttga caagaattgg cgcgggtgat ataataaata    60
cagtactgtt aactgcagga taagctt                                        87
```

<210> SEQ ID NO 16
<211> LENGTH: 2591
<212> TYPE: DNA
<213> ORGANISM: Bacillus subtilis
<220> FEATURE:
<221> NAME/KEY: CDS
<222> LOCATION: (997)..(2199)
<223> OTHER INFORMATION: MetE coding sequence

<400> SEQUENCE: 16

```
ggatccgctt tgaaatgcgg agcagaaaga atggtgaacg gctgctcaac tgttttctta    60
tcatttcctt ccggacggat aaacagctgc cgcgcaaata aattgtgcca tgcgaactca   120
tttacgacag tgatcggcag cctgtatttc tcgtctgctc cggcaaatcc ttcgaaaaca   180
aacagttcat ctcgctcctt taaatagctg acaactttcg tgtacagccg ctcaaacgct   240
tcttctgaaa tcggctgatt caccgggccc caatcgatct tatttttcgt gctttcttcc   300
tccacgatga atttatcttt aggtgagcgt cctgtgtaag cgcctgttgt cgcgcgaaca   360
gcacctgtgg atgttaaaat gccttcgttt cgggagagga cttttctgt tagctgtgct    420 gctgataaat tatgacgcac atttggacat gttaataagg cttgtgaatc agcggtcaaa   480
tcaactgagt tcatatgaaa ccttccttta tcgttttttg tgtttgcta attgtgaatt    540 agtataacat atattttcaa atagtctata ctatttattg tttttttgtgt gtgcatttcc  600 attgttttcc ctcaatatag gtgcctattt cttctgaatc atattgacat tgcaaaccct   660
tttacgataa gatatttcat tgagcggata ctcttatccc gagctggcgg agggacaggc   720
cctatgaagc ccagcaaccg gtttctctgt tatttattat gttcaattga gtgagacaac   780
caaggtgcta acctgttgca aggttgtatg attccttgag cgataagagt gaaaggcaca   840
aagaccaaac cctttcctcg atggaaaagg tttttttatt tcataaatat gccaattaac   900
attctctaat ataactgtac attgtataag agggagcgag ttccgtatca tatatacaag   960
gtctttcggg aggccttgtg caggaggaag caaatc atg agt aaa aat cgt cgt   1014
                                         Met Ser Lys Asn Arg Arg
                                         1               5 tta ttt aca tca gaa tct gtt acg gag ggg cat ccg gat aaa atc tgt   1062
Leu Phe Thr Ser Glu Ser Val Thr Glu Gly His Pro Asp Lys Ile Cys
        10                  15                  20 gac cag att tat gac agc att tta gat gaa att tta aag aaa gac cct   1110
Asp Gln Ile Tyr Asp Ser Ile Leu Asp Glu Ile Leu Lys Lys Asp Pro
    25                  30                  35 aac gcg cgt gtt gct tgt gaa aca tct gtg aca aca ggt ttg gtt ctt   1158
Asn Ala Arg Val Ala Cys Glu Thr Ser Val Thr Thr Gly Leu Val Leu
40                  45                  50 gta agc gga gag atc aca act tct acg tat gtt gac att ccg aaa acg   1206
Val Ser Gly Glu Ile Thr Thr Ser Thr Tyr Val Asp Ile Pro Lys Thr
55                  60                  65                  70
```

-continued

| | | |
|---|---|---|
| gtt cgc caa acc att aaa gaa atc gga tac aca cgt gca aaa tac gga<br>Val Arg Gln Thr Ile Lys Glu Ile Gly Tyr Thr Arg Ala Lys Tyr Gly<br>                     75                        80                     85 | 1254 |
| ttt gat gcg gaa act tgt gcg gtt tta aca tca att gat gag cag tct<br>Phe Asp Ala Glu Thr Cys Ala Val Leu Thr Ser Ile Asp Glu Gln Ser<br>             90                       95                      100 | 1302 |
| gct gat atc gcg atg ggc gta gac cca gcg ctt gaa gcc cgt gaa ggc<br>Ala Asp Ile Ala Met Gly Val Asp Pro Ala Leu Glu Ala Arg Glu Gly<br>            105                    110                    115 | 1350 |
| aca atg agc gac gaa gaa att gaa gcg att ggt gcg ggt gac caa gga<br>Thr Met Ser Asp Glu Glu Ile Glu Ala Ile Gly Ala Gly Asp Gln Gly<br>        120                    125                    130 | 1398 |
| tta atg ttc ggt tat gtg tgc aac gaa acg aaa gag ctt atg cct ctt<br>Leu Met Phe Gly Tyr Val Cys Asn Glu Thr Lys Glu Leu Met Pro Leu<br>135                      140                    145                    150 | 1446 |
| cca att tca ctt gcc cat aaa tta gcc cgc cgc cta agt gaa gtc cgt<br>Pro Ile Ser Leu Ala His Lys Leu Ala Arg Arg Leu Ser Glu Val Arg<br>                  155                    160                    165 | 1494 |
| aaa gaa gat att ctt ccg tac ctt cgc cct gac ggc aaa aca cag gta<br>Lys Glu Asp Ile Leu Pro Tyr Leu Arg Pro Asp Gly Lys Thr Gln Val<br>              170                    175                    180 | 1542 |
| acg gtt gag tac gat gaa aat aac aaa cca gtc cgc att gac gcg att<br>Thr Val Glu Tyr Asp Glu Asn Asn Lys Pro Val Arg Ile Asp Ala Ile<br>        185                    190                    195 | 1590 |
| gtt att tca act cag cat cac cct gaa att aca ctt gag caa att cag<br>Val Ile Ser Thr Gln His His Pro Glu Ile Thr Leu Glu Gln Ile Gln<br>        200                    205                    210 | 1638 |
| cgc aac att aaa gaa cat gta atc aat ccg gtt gtt cct gaa gag ctg<br>Arg Asn Ile Lys Glu His Val Ile Asn Pro Val Val Pro Glu Glu Leu<br>215                      220                    225                    230 | 1686 |
| att gat gaa gaa aca aaa tat ttc atc aac cct aca gga cgt ttc gta<br>Ile Asp Glu Glu Thr Lys Tyr Phe Ile Asn Pro Thr Gly Arg Phe Val<br>                  235                    240                    245 | 1734 |
| atc gga ggc cct caa ggg gat gcg gga ctt aca gga cgc aaa atc atc<br>Ile Gly Gly Pro Gln Gly Asp Ala Gly Leu Thr Gly Arg Lys Ile Ile<br>              250                    255                    260 | 1782 |
| gtt gat acg tac ggc ggc tat gca cgc cac ggc gga ggc gcg ttc tca<br>Val Asp Thr Tyr Gly Gly Tyr Ala Arg His Gly Gly Gly Ala Phe Ser<br>        265                    270                    275 | 1830 |
| ggt aag gac gcg acg aag gta gac cgt tct gca gct tat gcg gca aga<br>Gly Lys Asp Ala Thr Lys Val Asp Arg Ser Ala Ala Tyr Ala Ala Arg<br>280                      285                    290 | 1878 |
| tac gtt gcg aaa aac atc gtt gcg gct gag ctt gct gat tct tgc gaa<br>Tyr Val Ala Lys Asn Ile Val Ala Ala Glu Leu Ala Asp Ser Cys Glu<br>295                      300                    305                    310 | 1926 |
| gta cag ctt gct tac gcg atc ggt gtt gca cag cct gtg tca atc tca<br>Val Gln Leu Ala Tyr Ala Ile Gly Val Ala Gln Pro Val Ser Ile Ser<br>              315                    320                    325 | 1974 |
| atc aac aca ttc ggt tca gga aaa gct tct gag gaa aaa ctg att gaa<br>Ile Asn Thr Phe Gly Ser Gly Lys Ala Ser Glu Glu Lys Leu Ile Glu<br>            330                    335                    340 | 2022 |
| gtt gtt cgc aat aac ttt gat tta cga cct gcc gga att atc aaa atg<br>Val Val Arg Asn Asn Phe Asp Leu Arg Pro Ala Gly Ile Ile Lys Met<br>        345                    350                    355 | 2070 |
| ctt gat ttg cgc cgt ccg atc tat aaa caa act gct gcg tac ggc cac<br>Leu Asp Leu Arg Arg Pro Ile Tyr Lys Gln Thr Ala Ala Tyr Gly His<br>            360                    365                    370 | 2118 |
| ttt gga cgt cac gat gtt gac ctt cca tgg gag cgc aca gac aaa gcg<br>Phe Gly Arg His Asp Val Asp Leu Pro Trp Glu Arg Thr Asp Lys Ala<br>375                      380                    385                    390 | 2166 |

```
gag cag ctg cgt aaa gaa gcg tta gga gaa taa ttttatagcc gcttactggt    2219
Glu Gln Leu Arg Lys Glu Ala Leu Gly Glu
            395                 400 taagcggctt ccccttttt atcgttgtat tcatgtttat ttttttacat aactgcgaaa      2279
ccaaatacta ttcacagcgt ctataaatag gggttcaatg atgacaattt taattatgga    2339
ggcaatacta tgtgtggatt tgtcgggggtt tttaacaagc atccgttagc tcaaaccgct    2399
gatcaagaag aactaatcaa acaaatgaac caaatgatcg ttcaccgcgg tcctgacagt    2459
gatggatatt ccatgatga gcacgtcggc ttcggattca gacggctcag cattattgat     2519
gtagaaaatg gtggacagcc tttatcatat gaagatgaaa catattggat tatctttaac    2579
ggagtaaatc ta                                                         2591
```

<210> SEQ ID NO 17
<211> LENGTH: 400
<212> TYPE: PRT
<213> ORGANISM: Bacillus subtilis

<400> SEQUENCE: 17

```
Met Ser Lys Asn Arg Arg Leu Phe Thr Ser Glu Ser Val Thr Glu Gly
1               5                   10                  15

His Pro Asp Lys Ile Cys Asp Gln Ile Tyr Asp Ser Ile Leu Asp Glu
            20                  25                  30

Ile Leu Lys Lys Asp Pro Asn Ala Arg Val Ala Cys Glu Thr Ser Val
        35                  40                  45

Thr Thr Gly Leu Val Leu Ser Gly Glu Ile Thr Thr Ser Thr Tyr
    50                  55                  60

Val Asp Ile Pro Lys Thr Val Arg Gln Thr Ile Lys Glu Ile Gly Tyr
65                  70                  75                  80

Thr Arg Ala Lys Tyr Gly Phe Asp Ala Glu Thr Cys Ala Val Leu Thr
                85                  90                  95

Ser Ile Asp Glu Gln Ser Ala Asp Ile Ala Met Gly Val Asp Pro Ala
            100                 105                 110

Leu Glu Ala Arg Glu Gly Thr Met Ser Asp Glu Glu Ile Glu Ala Ile
        115                 120                 125

Gly Ala Gly Asp Gln Gly Leu Met Phe Gly Tyr Val Cys Asn Glu Thr
    130                 135                 140

Lys Glu Leu Met Pro Leu Pro Ile Ser Leu Ala His Lys Leu Ala Arg
145                 150                 155                 160

Arg Leu Ser Glu Val Arg Lys Glu Asp Ile Leu Pro Tyr Leu Arg Pro
                165                 170                 175

Asp Gly Lys Thr Gln Val Thr Val Glu Tyr Asp Glu Asn Asn Lys Pro
            180                 185                 190

Val Arg Ile Asp Ala Ile Val Ile Ser Thr Gln His His Pro Glu Ile
        195                 200                 205

Thr Leu Glu Gln Ile Gln Arg Asn Ile Lys Glu His Val Ile Asn Pro
    210                 215                 220

Val Val Pro Glu Glu Leu Ile Asp Glu Thr Lys Tyr Phe Ile Asn
225                 230                 235                 240

Pro Thr Gly Arg Phe Val Ile Gly Gly Pro Gln Gly Asp Ala Gly Leu
                245                 250                 255

Thr Gly Arg Lys Ile Ile Val Asp Thr Tyr Gly Gly Tyr Ala Arg His
            260                 265                 270
```

-continued

```
Gly Gly Gly Ala Phe Ser Gly Lys Asp Ala Thr Lys Val Asp Arg Ser
        275             280             285

Ala Ala Tyr Ala Ala Arg Tyr Val Ala Lys Asn Ile Val Ala Ala Glu
    290             295             300

Leu Ala Asp Ser Cys Glu Val Gln Leu Ala Tyr Ala Ile Gly Val Ala
305             310             315             320

Gln Pro Val Ser Ile Ser Ile Asn Thr Phe Gly Ser Gly Lys Ala Ser
            325             330             335

Glu Glu Lys Leu Ile Glu Val Val Arg Asn Asn Phe Asp Leu Arg Pro
            340             345             350

Ala Gly Ile Ile Lys Met Leu Asp Leu Arg Arg Pro Ile Tyr Lys Gln
        355             360             365

Thr Ala Ala Tyr Gly His Phe Gly Arg His Asp Val Asp Leu Pro Trp
    370             375             380

Glu Arg Thr Asp Lys Ala Glu Gln Leu Arg Lys Glu Ala Leu Gly Glu
385             390             395             400
```

METHOD FOR STABLE GENE-AMPLIFICATION IN A BACTERIAL HOST CELL

CROSS-REFERENCE TO RELATED APPLICATIONS

This application is a divisional of U.S. application Ser. No. 14/180,975 filed on Feb. 14, 2014, now U.S. Pat. No. 9,458,468, which is a continuation of U.S. application Ser. No. 12/712,537 filed on Feb. 25, 2010, now U.S. Pat. No. 8,685,653, which is a continuation of U.S. application Ser. No. 10/575,697 filed on Apr. 12, 2006, now U.S. Pat. No. 7,700,322, which is a 35 U.S.C. 371 national phase application of international application no. PCT/DK2004/000750 filed on Oct. 29, 2004, which claims priority or the benefit under 35 U.S.C. 119 of Danish application no. PA 2003 01624 filed on Oct. 31, 2003 and U.S. provisional application No. 60/518,916 filed on Nov. 10, 2003. The content of these applications is fully incorporated herein by reference.

FIELD OF THE INVENTION

In the biotech industry it is desirable to construct polypeptide production strains having several copies of a gene of interest stably chromosomally integrated, without leaving antibiotic resistance marker genes in the strains.

This invention relates to bacterial host cells comprising at least two copies of an amplification unit in its genome, said amplification unit comprising: i) at least one copy of a gene of interest, and ii) an expressible conditionally essential gene, wherein the conditionally essential gene is either promoterless or transcribed from a heterologous promoter having an activity substantially lower than the endogenous promoter of said conditionally essential gene, and wherein the conditionally essential gene if not functional would render the cell auxotrophic for at least one specific substance or unable to utilize one or more specific sole carbon source; methods for producing a protein using the cell of the invention, and methods for constructing the cell of the invention.

BACKGROUND OF THE INVENTION

In the industrial production of polypeptides it is of interest to achieve a product yield as high as possible. One way to increase the yield is to increase the copy number of a gene encoding a polypeptide of interest. This can be done by placing the gene on a high copy number plasmid, however plasmids are unstable and are often lost from the host cells if there is no selective pressure during the cultivation of the host cells. Another way to increase the copy number of the gene of interest is to integrate it into the host cell chromosome in multiple copies.

The present day public debate concerning the industrial use of recombinant DNA technology has raised some questions and concerns about the use of antibiotic resistance marker genes. Antibiotic marker genes are traditionally used as a means to select for strains carrying multiple copies of both the marker genes and an accompanying expression cassette coding for a polypeptide of industrial interest. In order to comply with the current demand for recombinant production host strains devoid of antibiotic markers, we have looked for possible alternatives to the present technology that will allow substitution of the antibiotic markers we use today with non-antibiotic marker genes.

WO 02/00907 (Novozymes, Denmark) discloses a method for stable chromosomal multi-copy integration of genes into a production host cell in specific well-defined sites. It is disclosed to first render a recipient cell deficient by inactivating one or more conditionally essential gene, e.g., to make the cell auxotrophic for an amino acid. A gene of interest may then be integrated into the chromosome along with a DNA sequence which complements the deficiency of the cell, thus making the resulting cell selectable; the Bacillus licheniformis metC gene is disclosed as a conditionally essential marker herein.

WO 01/90393 (Novozymes, Denmark) discloses a method for increasing the gene copy number in a host cell by gene-amplification, without leaving antibiotic resistance markers behind in the host cell. The disclosed method relies on rendering a specific type of conditionally essential chromosomal gene of the host cell non-functional. A single amplification unit comprising the gene of interest, and a DNA sequence, which when integrated into the chromosome complements the non-functional conditional essential chromosomal gene, is integrated into the chromosome.

In order to provide recombinant production strains devoid of antibiotic resistance markers, it remains of industrial interest to find new methods to stably integrate genes in multiple copies into host cell chromosomes. Even incremental improvements of existing methods or mere alternatives are of considerable interest to the industry.

SUMMARY OF THE INVENTION

The problem to be solved by the present invention is to provide alternative host cells comprising multiple copies of a gene of interest, which cells are devoid of antibiotic markers, for use in the industrial production of polypeptides in high yields.

The solution is based on the observation that an amplification unit can be integrated into the chromosome of a host cell, and subsequently be amplified, without the use of classical antibiotic markers, antibiotics, or endogenously produced inhibitory compounds.

In traditional amplification protocols, higher gene expression is a result of duplications of the antibiotic resistance marker gene, duplications which are selected in stepwise cultivation and selection rounds by adding increasing amounts of the antibiotic compound to the cultivation medium in each cultivation step.

A cell which has become auxotrophic, e.g., due to a non-functional conditionally essential gene, would normally be complemented back to the prototrophic phenotype by the integration (or restoration) in the chromosome of even one single functional copy of the non-functional gene. Since normally only one copy is needed, such genes have not previously been attractive candidates for amplification purposes.

However, the present inventors lowered the expression-level of a non-antibiotic conditionally essential gene by decreasing the promoter activity, so that more than one functional copy of the gene would be advantageous to a deficient host cell. The integration of an amplification unit comprising such a low-level expression conditionally essential gene, into a host cell deficient for the same gene, reproducibly resulted in genomic duplications of the integrated amplification unit, comparable to what has been observed when using traditional amplifiable antibiotic markers.

In fact, this invention provides the means for controlling the level of gene expression, i.e., copy-number, in a host cell.

By choosing carefully the strength of the heterologous promoter expressing the conditionally essential marker gene in the amplification unit, the optimal copy-number of the amplification unit can be adjusted up or down, depending on the desired expression level of the gene of interest also comprised in the unit.

Accordingly, in a first aspect the invention relates to a bacterial host cell comprising at least two copies of an amplification unit in its genome, said amplification unit comprising:

i) at least one copy of a gene of interest, and
ii) an expressible conditionally essential gene, wherein the conditionally essential gene is either promoterless or transcribed from a heterologous promoter having an activity substantially lower than the endogenous promoter of said conditionally essential gene, and wherein the conditionally essential gene if not functional would render the cell auxotrophic for at least one specific substance or unable to utilize one or more specific sole carbon source.

In a second aspect, the invention relates to a method for producing a protein encoded by a gene of interest, comprising a) culturing a bacterial host cell comprising at least two duplicated copies of an amplification unit in its genome, the amplification unit comprising:
i) at least one copy of the gene of interest, and
ii) an expressible conditionally essential gene, wherein the conditionally essential gene is either promoterless or transcribed from a heterologous promoter having an activity substantially lower than the endogenous promoter of said conditionally essential gene,
wherein the conditionally essential gene if not functional would render the cell auxotrophic for at least one specific substance or unable to utilize one or more specific sole carbon source; and
b) recovering the protein.

In a final aspect, the invention also relates to a method for producing a bacterial cell comprising two or more amplified chromosomal copies of a gene of interest, the method comprising:

a) providing a bacterial cell comprising at least one copy of an amplification unit, the unit comprising:
i) at least one copy of the gene of interest, and
ii) an expressible functional copy of a conditionally essential gene, which is either promoterless or transcribed from a heterologous promoter having an activity substantially lower than the endogenous promoter of said conditionally essential gene, wherein the conditionally essential gene if not functional would render the cell auxotrophic for at least one specific substance or unable to utilize one or more specific sole carbon source;
b) cultivating the cell under conditions suitable for growth in a medium deficient of said at least one specific substance and/or with said one or more specific sole carbon source, thereby providing a growth advantage to a cell in which the amplification unit has been duplicated in the chromosome; and
c) selecting a cell wherein the amplification unit has been duplicated in the chromosome, whereby two or more amplified chromosomal copies of the gene of interest were produced.

It is envisioned that all the preferred embodiments of the cell of the invention that are shown herein would be suitable for use in the methods of the second and third aspects of the invention.

Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989") DNA Cloning: A Practical Approach, Volumes I and II /D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "nucleic acid molecule" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

A DNA "coding sequence" or an "open reading frame (ORF)" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "secretory signal sequence" is a DNA sequence that encodes a polypeptide (a "secretory peptide" that, as a component of a larger polypeptide, directs the larger polypeptide through a secretory pathway of a cell in which it is synthesized. The larger polypeptide is commonly cleaved to remove the secretory peptide during transit through the secretory pathway.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A chromosomal gene is rendered non-functional if the polypeptide that the gene encodes can no longer be expressed in a functional form. Such non-functionality of a gene can be induced by a wide variety of genetic manipulations as known in the art, some of which are described in Sambrook et al. vide supra. Partial deletions within the ORF of a gene will often render the gene non-functional, as will mutations.

The term "an expressible copy of a chromosomal gene" is used herein as meaning a copy of the ORF of a chromosomal gene, wherein the ORF can be expressed to produce a fully functional gene product. The expressible copy may not be transcribed from the native promoter of the chromosomal gene, it may instead be transcribed from a foreign or heterologous promoter, or it may indeed be promoterless and expressed only by transcriptional read-through from a gene present upstream of the 5' end of the ORF. Transcriptional read-through is intended to have the same meaning here as the generally recognized meaning in the art.

"Operably linked", when referring to DNA segments, indicates that the segments are arranged so that they function in concert for their intended purposes, e.g., transcription initiates in the promoter and proceeds through the coding segment to the terminator.

A coding sequence is "under the control" of transcriptional and translational control sequences in a cell when RNA polymerase transcribes the coding sequence into mRNA, which is then trans-RNA spliced and translated into the protein encoded by the coding sequence.

"Heterologous" DNA refers to DNA not naturally located in the cell, or in a chromosomal site of the cell. Preferably, the heterologous DNA includes a gene foreign to the cell.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a polypeptide of interest. The construct may optionally contain other nucleic acid segments.

The nucleic acid construct of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The nucleic acid construct of the invention encoding the polypeptide may also be prepared synthetically by established standard methods, e.g., the phosphoamidite method described by Beaucage and Caruthers, 1981, *Tetrahedron Letters* 22: 1859-1869, or the method described by Matthes et al., 1984, *EMBO Journal* 3: 801-805. According to the phosphoamidite method, oligonucleotides are synthesized, e.g., in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques. The nucleic acid construct may also be prepared by polymerase chain reaction using specific primers, for instance as described in U.S. Pat. No. 4,683,202 or Saiki et al., 1988, Science 239: 487-491.

The term nucleic acid construct may be synonymous with the term "expression cassette" when the nucleic acid construct contains the control sequences necessary for expression of a coding sequence of the present invention The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription and translation control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the expressed polypeptide into the cell's secretory pathway of the host cell. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. A foreign signal peptide coding region may be required where the coding sequence does not normally contain a signal peptide coding region. Alternatively, the foreign signal peptide coding region may simply replace the natural signal peptide coding region in order to obtain enhanced secretion of the enzyme relative to the natural signal peptide coding region normally associated with the coding sequence. The signal peptide coding region may be obtained from a glucoamylase or an amylase gene from an *Aspergillus* species, a lipase or proteinase gene from a *Rhizomucor* species, the gene for the alpha-factor from *Saccharomyces cerevisiae,* an amylase or a protease gene from a *Bacillus* species, or the calf preprochymosin gene. However, any signal peptide coding region capable of directing the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Examples of suitable promoters for directing the transcription of the conditionally essential gene(s) of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus subtilis* alkaline protease gene, the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus amyloliquefaciens* BAN amylase gene, the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American* 242: 74-94 (1980); and in Sambrook et al., 1989, supra.

The term "auxotrophic" in the present context means that the auxotrophic cell requires at least one specific substance for growth and metabolism that the parental organism was able to synthesize on its own. The term is used with respect to organisms, such as strains of bacteria, that can no longer synthesize the substance(s) because of mutational changes.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, *Microbiological Reviews* 57: 109-137.

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Antibiotic selectable markers confer antibiotic resistance to such antibiotics as ampicillin, kanamycin, chloramphenicol, tetracycline, neomycin, hygromycin or methotrexate. Suitable markers for yeast host cells are ADE2, HIS3, LEU2, LYS2, MET3, TRP1, and URA3.

The vectors of the present invention preferably contain an element(s) that permits stable integration of the vector, or of a smaller part of the vector, into the host cell genome or autonomous replication of the vector in the cell independent of the genome of the cell.

The vectors, or smaller parts of the vectors such as amplification units of the present invention, may be integrated into the host cell genome when introduced into a host cell. For chromosomal integration, the vector may rely on the nucleic acid sequence encoding the polypeptide or any other element of the vector for stable integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences; specific examples of encoding sequences suitable for site-specific integration by homologous recombination are given in WO 02/00907 (Novozymes, Denmark), which is hereby incorporated by reference in its totality.

On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences. The copy number of a vector, an expression cassette, an amplification unit, a gene or indeed any defined nucleotide sequence is the number of identical copies that are present in a host cell at any time. A gene or another defined chromosomal nucleotide sequence may be present in one, two, or more copies on the chromosome. An autonomously replicating vector may be present in one, or several hundred copies per host cell.

An amplification unit of the invention is a nucleotide sequence that can integrate into the chromosome of a host cell, whereupon it can increase in number of chromosomally integrated copies by duplication of multiplication. The unit comprises an expression cassette as defined herein comprising at least one copy of a gene of interest and an expressable copy of a chromosomal gene, as defined herein, of the host cell. When the amplification unit is integrated into the chromosome of a host cell, it is defined as that particular region of the chromosome which is prone to being duplicated by homologous recombination between two directly repeated regions of DNA. The precise border of the amplification unit with respect to the flanking DNA is thus defined functionally, since the duplication process may indeed duplicate parts of the DNA which was introduced into the chromosome as well as parts of the endogenous chromosome itself, depending on the exact site of recombination within the repeated regions. This principle is illustrated in Janniére et al. (1985, Stable gene amplification in the chromosome of *Bacillus subtilis*. Gene, 40: 47-55), which is incorporated herein by reference.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMbetal. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The transformation of a bacterial host cell may, for instance, be effected by protoplast transformation (see, e.g., Chang and Cohen, 1979, *Molecular General Genetics* 168: 111-115), by using competent cells (see, e.g., Young and Spizizin, 1961, *Journal of Bacteriology* 81: 823-829, or Dubnar and Davidoff-Abelson, 1971, Journal of Molecular Biology 56:209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5771-5278).

The transformed or transfected host cells described above are cultured in a suitable nutrient medium under conditions permitting the expression of the desired polypeptide, after which the resulting polypeptide is recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g., in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991).

If the polypeptide is secreted into the nutrient medium, the polypeptide can be recovered directly from the medium. If the polypeptide is not secreted, it is recovered from cell lysates. The polypeptide are recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, gel filtration chromatography, affinity chromatography, or the like, dependent on the type of polypeptide in question.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

DETAILED DESCRIPTION OF THE INVENTION

The first aspect of the invention relates to a bacterial host cell comprising at least two copies of an amplification unit in its genome, said amplification unit comprising:
 i) at least one copy of a gene of interest, and
 ii) an expressible conditionally essential gene, wherein the conditionally essential gene is either promoterless or transcribed from a heterologous promoter having an activity substantially lower than the endogenous promoter of said conditionally essential gene, and wherein the conditionally essential gene if not functional would render the cell auxotrophic for at least one specific substance or unable to utilize one or more specific sole carbon source.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In one preferred embodiment, the bacterial host cell is a prokaryotic cell, preferably a a Gram-positive prokaryotic cell, and more preferably the bacterial Gram positive cell is a species of the genus *Bacillus*, preferably selected from the group consisting of *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis*.

As described above, chromosomal integration of a vector or a smaller part of a vector, such as an amplification unit of the invention, into the genome of the host cell can be achieved by a number of ways. A non-limiting example of integration by homologous recombination is shown herein.

A preferred embodiment of the invention relates to the cells of the invention, or the methods of the invention, wherein the amplification unit further comprises a nucleotide sequence with a homology to a chromosomal nucleotide sequence of the host cell sufficient to effect chromosomal integration in the host cell of the amplification unit by homologous recombination, preferably the amplification unit further comprises a nucleotide sequence of at least 100 bp, preferably 200 bp, more preferably 300 bp, even more preferably 400 bp, and most preferably at least 500 bp with an identity of at least 70%, preferably 80%, more preferably 90%, even more preferably 95%, and most preferably at least 98% identity to a chromosomal nucleotide sequence of the host cell.

In a non-limiting example integration into the chromosome of a host cell can be selected for by first rendering a conditionally essential host cell gene non-functional as described elsewhere herein, thereby rendering the host cell selectable, then targetting the vector's integration by including on this a likewise non-functional copy of same host gene of a size that allows homologous recombination between the two different copies of the non-functional host genes in the genome of the host cell and on the integration vector, tailored so that such a recombination will restore a functional copy of the gene, thus leaving the host cell selectable. Or the vector may simply comprise a functional copy of the conditionally essential gene, to select for integration anywhere in the genome.

A preferred embodiment of the invention relates to the cell of the invention, wherein a first amplification unit integrates into the host cell chromosome by homologous recombination with the partially deleted conditionally essential gene and renders the gene functional.

A preferred embodiment of the invention relates to the cell of the invention, wherein the gene of interest encodes a polypeptide of interest, preferably the polypeptide is an enzyme such as a protease; a cellulase; a lipase; a xylanase; a phospholipase; or preferably an amylase.

Another preferred embodiment of the invention relates to the cell of the invention, wherein the polypeptide is a hormone, a pro-hormone, a pre-pro-hormone, a small peptide, a receptor, or a neuropeptide.

Still another preferred embodiment of the invention relates to the cell of the invention, wherein the gene of interest encodes an enzyme, preferably an amylolytic enzyme, a lipolytic enzyme, a proteolytic enzyme, a cellulytic enzyme, an oxidoreductase or a plant cell-wall degrading enzyme, and more preferably an enzyme with an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase.

In a preferred embodiment, the invention relates to a cell, wherein the gene of interest encodes an antimicrobial peptide, preferably an anti-fungal peptide or an anti-bacterial peptide, or a peptide with biological activity in the human body, preferably a pharmaceutically active peptide, more preferably insulin/pro-insulin/pre-pro-insulin or variants thereof, growth hormone or variants thereof, or blood clotting factor VII or VIII or variants thereof.

Conditionally essential genes are well-characterized in the literature, for instance genes that are required for a cell to synthesize one or more amino acids, where a non-functional gene encoding a polypeptide required for synthesis of an amino acid renders the cell auxotrophic for that amino acid, and the cell can only grow if the amino acid is supplied to the growth medium. Restoration of the functionality of such a gene, or complementation by providing an exogenous functional copy of such a gene, allows the cell to synthesise the amino acid on its own, and it becomes selectable against a background of auxotrophic cells.

Consequently, a preferred embodiment of the invention relates to a cell of the first aspect, wherein the conditionally essential chromosomal gene(s) of the host cell encodes one or more polypeptide(s) involved in amino acid synthesis, and the non-functionality of the endogenous versions of the gene(s) renders the cell auxotrophic for one or more amino acid(s), and wherein restoration of the functionality of the gene(s) renders the cell prototrophic for the amino acid(s).

*Bacillus subtilis* metE encodes a S-adenosyl-methionine synthetase, the metE/MetE sequences are available from EMBL:BS52812 (accession no. U52812) (Yocum et al., 1996, Cloning and characterization of the metE gene encoding S-adenosylmethionine synthetase from *Bacillus subtilis*, *J. Bacteriol.* 178(15): 4604).

The leuB gene encodes 3-isopropylmalate dehydrogenase, which catalyses the conversion of 3-carboxy-2-hydroxy-4-methylpentanoate to 3-carboxy-4-methyl-2-oxopentanoate. A leuB-deficient strain will be a leucine auxotroph.

The lysA gene encoding diaminopimelate decarboxylase, which catalyses the conversion of Meso-2,6-diaminoheptanedioate to L-lysine. A lysA-deficient strain will be a lysine auxotroph.

A preferred embodiment relates to a cell of the invention, wherein the conditionally essential gene encodes an enzyme from the biosynthetic pathway of an amino acid; preferably the conditionally essential gene encodes one or more polypeptide(s) involved in lysine, leucine or methionine synthesis, preferably the conditionally essential gene is homologous to the lysA, leuB, metC, or the metE gene from *Bacillus subtilis*, and more preferably the conditionally essential gene is the lysA, leuB, metC, or metE gene from *Bacillus licheniformis*; more preferably the conditionally essential gene is at least 75% identical, preferably 85% identical, more preferably 95% and most preferably at least 97% identical to the lysA sequence of *Bacillus licheniformis* shown in SEQ ID NO:48 of WO 02/00907, the leuB sequence of *Bacillus licheniformis*, the metC sequence of *Bacillus licheniformis* shown in SEQ ID NO:42 of WO 02/00907, or the metE sequence of *Bacillus subtilis* shown in positions 997 to 2199 of SEQ ID NO:16.

The hemA gene encodes glutamyl-tRNA reductase, which catalyses the synthesis of 5-amino leuvulinic acid. A hemA-deficient strain will have to be supplemented with 5-amino leuvulinic acid or haemin.

In another embodiment, the conditionally essential gene encodes a glutamyl-tRNA reductase, preferably the conditionally essential gene is homologous to the hemA gene from *Bacillus subtilis*, and more preferably the conditionally essential gene is the hemA gene from *Bacillus licheniformis*; preferably the conditionally essential gene is at least 75% identical, preferably 85% identical, more preferably 95% and most preferably at least 97% identical to the hemA sequence of *Bacillus licheniformis*.

The conditionally essential gene(s) may encode polypeptides involved in the utilization of specific carbon sources such as xylose, glucanate, glycerol, or arabinose, in which case the host cell is unable to grow in a minimal medium supplemented with only that specific carbon source when the gene(s) are non-functional.

A preferred embodiment of the invention relates to a cell of the invention, wherein the at least one conditionally essential chromosomal gene(s) is one or more genes that are required for the host cell to grow on minimal medium supplemented with only one specific main carbon-source.

A preferred embodiment relates to a cell of the invention, wherein the at least one conditionally essential gene encodes an enzyme required for xylose utilization, preferably the conditionally essential gene is homologous to the xylA gene from *Bacillus subtilis*, and more preferably the conditionally essential gene is homologous to a gene of the xylose isomerase operon of *Bacillus licheniformis*, most preferably to the xylA gene of *Bacillus licheniformis*; preferably the conditionally essential gene encodes a xylose isomerase and is at least 75% identical, preferably 85% identical, more preferably 95% and most preferably at least 97% identical to the xylA gene of *Bacillus licheniformis*.

Another preferred embodiment relates to a cell of the invention, wherein the at least one conditionally essential gene encodes an enzyme required for gluconate utilization, preferably the conditionally essential gene encodes a gluconate kinase (EC 2.7.1.12) or a gluconate permease, more preferably the gene is homologous to the gntK gene or the gntP gene from *Bacillus subtilis*, and most preferably the gene is the gntK or gntP gene from *Bacillus licheniformis*; preferably the conditionally essential gene encodes a gluconate kinase (EC 2.7.1.12) or a gluconate permease or both and is at least 75% identical, preferably 85% identical, more preferably 95% and most preferably at least 97% identical to any of the gntK and gntP sequences of *Bacillus licheniformis*.

Still another preferred embodiment relates to a cell of the invention, wherein the conditionally essential gene encodes an enzyme required for glycerol utilization, preferably the conditionally essential gene encodes a glycerol uptake facilitator (permease), a glycerol kinase, or a glycerol dehydrogenase, more preferably the conditionally essential gene is homologous to the glpP, glpF, glpK, or the glpD gene from *Bacillus subtilis*, and most preferably the conditionally essential gene comprises one or more of the glpP, glpF, glpK, and glpD genes from *Bacillus licheniformis* shown in SEQ ID NO:26 of WO 02/00907 (Novozymes A/S) which is incorporated herein by reference in its totality; preferably the conditionally essential gene encodes a glycerol uptake facilitator (permease), a glycerol kinase, or a glycerol dehydrogenase, and is at least 75% identical, preferably 85% identical, more preferably 95% and most preferably at least 97% identical to any of the glpP, glpF, glpK, and glpD sequences of *Bacillus licheniformis* shown in SEQ ID NO:26 of WO 02/00907.

One more preferred embodiment relates to a cell of the invention, wherein the conditionally essential gene encodes an enzyme required for arabinose utilization, preferably an arabinose isomerase, more preferably the gene is homologous to the araA gene from *Bacillus subtilis*, and most preferably the gene is the araA gene from *Bacillus licheniformis* shown in SEQ ID NO:38 of WO 02/00907; preferably the conditionally essential gene encodes an arabinose isomerase, and is at least 75% identical, preferably 85% identical, more preferably 95% and most preferably at least 97% identical to the araA sequence of *Bacillus licheniformis* shown in SEQ ID NO:38 of WO 02/00907.

The amplification unit in the cell of the invention may also include an antibiotic marker gene. However, as it is preferred not to have marker genes in the chromosome, an alternative way of removing the marker gene must be employed. Specific restriction enzymes denoted resolvases excise portions of DNA if each portion is flanked on both sides by certain recognition sequences known as resolvase sites or res-sites; these resolvase enzymes are well-known in the art, see, e.g., WO 96/23073 (Novo Nordisk A/S) which is included herein by reference.

A preferred embodiment relates to a cell of the invention, wherein the amplification unit further comprises an antibiotic selection marker, preferably the selection marker is flanked by resolvase sites or res-sites.

Subsequent to the action of the resolvase enzyme, the antibiotic restriction marker flanked by res-sites will have been excised from the chromosome of the cell, leaving only one copy of the res-site behind as testimony to the procedure.

Accordingly, a preferred embodiment relates to a cell of the invention, wherein the amplification unit further comprises a resolvase site or res-site.

As the present invention relies on a reduced transcription of the conditionally essential gene comprised in the amplification unit as compared to its wild-type transcription level, it may be an advantage to include one or more transcription terminators upstream of the gene in different reading frames, in order to avoid any unintentional read-through transcription from a gene further upstream in the chromosome from where the unit was integrated.

A preferred embodiment relates to a cell of the invention, wherein the conditionally essential gene comprised in the amplification unit has at least one transcription terminator located upstream of the gene.

Another way of reducing transcription of the conditionally essential gene is to express it from a heterologous or completely artificial promoter, which has a reduced activity as compared to the wild-type or endogenous promoter normally transcribing said gene. Preferably, the conditionally essential gene is transcribed from a heterologous promoter having an activity level, when compared with the endogenous promoter of the conditionally essential gene, which is reduced with a factor of 2, preferably 5, more preferably 10, even more preferably 50, and most preferably with a factor of 100.

Still another strategy could be to have a promoterless conditionally essential gene in the amplification unit, and then simply rely on what read-through transcription there might from any other gene(s) located upstream of the conditionally essential gene, before or after integration of the unit into the chromosome of the cell of the invention. Preferably, the conditionally essential gene is promoterless; and more preferably the gene of interest is located upstream of the conditionally essential gene in the amplification unit, so that the two genes are co-directionally transcribed, whereby the conditionally essential gene is expressed by read-through transcription from the gene of interest.

A second aspect of the invention relates to a method for producing a protein encoded by a gene of interest, comprising
a) culturing a bacterial host cell comprising at least two duplicated copies of an amplification unit in its genome, the amplification unit comprising:
  i) at least one copy of the gene of interest, and
  ii) an expressible conditionally essential gene, wherein the conditionally essential gene is either promoterless or transcribed from a heterologous promoter having an activity substantially lower than the endogenous promoter of said conditionally essential gene,
  wherein the conditionally essential gene if not functional would render the cell auxotrophic for at least one specific substance or unable to utilize one or more specific sole carbon source; and
b) recovering the protein.

As already mentioned, any cell of the invention is envisioned to be suitable in the methods of the second aspect, in particular the preferred embodiments outlined in the above.

A final aspect of the invention relates to methods for producing a bacterial cell comprising two or more amplified chromosomal copies of a gene of interest, the method comprising:
a) providing a bacterial cell comprising at least one copy of an amplification unit, the unit comprising:
  i) at least one copy of the gene of interest, and
  ii) an expressible functional copy of a conditionally essential gene, which is either promoterless or transcribed from a heterologous promoter having an activity substantially lower than the endogenous promoter of said conditionally essential gene, wherein the conditionally essential gene if not functional would render the cell auxotrophic for at least one specific substance or unable to utilize one or more specific sole carbon source;
b) cultivating the cell under conditions suitable for growth in a medium deficient of said at least one specific substance and/or with said one or more specific sole carbon source, thereby providing a growth advantage to a cell in which the amplification unit has been duplicated in the chromosome; and
c) selecting a cell wherein the amplification unit has been duplicated in the chromosome, whereby two or more amplified chromosomal copies of the gene of interest were produced.

Again, as already mentioned, the methods of the final aspect of the invention are envisioned as being suitable for producing any cell of the invention, in particular the preferred embodiments of said cell that are outlined in the above.

EXAMPLES

Strains and Donor Organisms

*Bacillus subtilis* PL1801. This strain is the *B. subtilis* DN1885 with disrupted apr and npr genes (Diderichsen et al., 1990, "Cloning of aldB, which encodes alpha-acetolactate decarboxylase, an exoenzyme from *Bacillus brevis*", *J. Bacteriol.* 172: 4315-4321).

*B. subtilis* CLO46. This strain is a *B. subtilis* PL1801 where the metE gene is deleted and replaced with the kanamycine (kan) resistance gene from pUB110 by use of the plasmid pCLO43.

*B. subtilis* CLO49. This strain is the CLO46 strain where the kanamycine resistance gene is deleted.

Competent cells were prepared and transformed as described by Yasbin et al., 1975, "Transformation and transfection in lysogenic strains of *Bacillus subtilis*: evidence for selective induction of prophage in competent cells", *J. Bacteriol.* 121: 296-304.

Plasmids pCLO43:

This plasmid is a pBR322 derivative (Watson, 1988, *Gene* 70(2): 399-403) essentially containing elements making the plasmid propagatable in *E. coli*, a ampicillin resistance gene, a gene conferring resistance to kanamycine, two flanking fragments from *B. subtilis* metE inserted upstream and downstream of the kanamycine resistance gene, two direct repeats that signify the res site from pAMBeta1 (Janniere, 1996, *Nucleic Acids Res.* 24(17): 3431-3436. This plasmid is used for deleting the metE gene in the *B. subtilis* strain PL1801.

TABLE 1

Plasmid pCLO43, 7311 bp

| Position (bp) | Size (bp) | Element (bp) | Origin |
| --- | --- | --- | --- |
| 1-973 | 973 | Upstream metE seq. | *B. subtilis* |
| 974-1010 | 37 | Linker | Synthetic |
| 10111-1184 | 174 | res site from pAMbeta1 | *E. faecalis* |
| 1185-1190 | 6 | Linker | Synthetic |
| 1191-2159 | 969 | pUB110 (Kan gene) | *S. aureus* |
| 2160-2162 | 3 | Linker | Synthetic |
| 2163-2336 | 174 | res site from pAMβ1 | *E. faecalis* |
| 2337-2357 | 21 | Linker | Synthetic |
| 2358-3870 | 1513 | Downstream metE seq. | *B. subtilis* |
| 3871-7311 | 3441 | PBR322 | *E. coli* | pCLO1154

This plasmid is a pBR322 derivative (Watson, 1988, *Gene* 70(2): 399-403) containing elements making the plasmid propagatable in *E. coli*. The plasmid codes for the ampicillin resistance gene, the kanamycine resistance gene, the chloramphenicol resistance gene and the lacZ gene from *E. coli*. The gfp gene from *A. victoria* and the metE gene from *B. subtilis* are transcriptionally fused in the plasmid controlled by a promoter that can be exchanged with other promoters. This plasmid is used for integration and amplification studies in the amyE locus of CLO49. The primers for metE fragment PCR amplifications on chromosomal DNA isolated from PL1801 are as follows:

```
P52 (SEQ ID NO: 1):
aataataaagatctggaggagaaacaatgacaacc

P53 (SEQ ID NO: 2):
aaataataagatctaaattatactagctgtgtc
```

TABLE 2

Plasmid pCLO1154, 13135 bp

| Position (bp) | Size (bp) | Element (bp) | Origin |
| --- | --- | --- | --- |
| 1-539 | 539 | Upstream amyE | *B. subtilis* |
| 540-2853 | 2314 | metE gene | *B. subtilis* |
| 2854-2891 | 38 | Linker | Synthetic |
| 2892-3605 | 714 | gfp gene | *A. victoria* |
| 3606-3739 | 134 | Promoter - alr | *B. subtilis* |
| 3740-3785 | 46 | Linker | Synthetic |
| 3786-4821 | 1036 | pC194 (cat gene) | *S. aureus* |
| 4822-5008 | 187 | part of tetC gene | *E. coli* |
| 5009-5106 | 98 | Promoter | Synthetic |
| 5107-5111 | 6 | Linker | Synthetic |
| 5112-8224 | 3113 | spoVG-lacZ fusion | *B. subtilis* & *E. coli* |
| 8226-8314 | 89 | part of tetC gene | *E. coli* |
| 8315-9657 | 1343 | Downstream amyE | *B. subtilis* |
| 9658-9845 | 188 | Linker | Synthetic |
| 9846-11117 | 1272 | pUB110 (neo gene) | *S. aureus* |
| 11118-11184 | 67 | Linker | Synthetic |

TABLE 2-continued

Plasmid pCLO1154, 13135 bp

| Position (bp) | Size (bp) | Element (bp) | Origin |
| --- | --- | --- | --- |
| 11185-11277 | 93 | Tn5 fragment | *E. coli* |
| 11278-11281 | 4 | Linker | Synthetic |
| 11282-13119 | 1838 | pBR322 (bla gene) | *E. coli* |
| 13120-13129 | 10 | Linker | Synthetic |

Propagation of PL1801 Strain for LacZ Activity Determination

The *B. subtilis* strain PL1801 was propagated in liquid medium TY. After 10 generations of incubation at 37° C. and 300 rpm, the cells were harvested, and cells were disrupted by sonic or lysozyme treatment.

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers (e.g., restriction endonucleases, ligases etc. are obtainable from New England Biolabs, Inc.).

Media

TY: (as described in Ausubel, F. M. et al. (eds.) "Current protocols in Molecular Biology". John Wiley and Sons, 1995). LB agar (as described in Ausubel, F. M. et al. (eds.) "Current protocols in Molecular Biology". John Wiley and Sons, 1995).

Minimal TSS agar: As described in Fouet and Sonenshein, 1990, "A Target for Carbon Source-Dependant Negative Regulation of the citB Promoter of Bacillus subtilis", *J. Bacteriol.* 172: 835-844. For plates, 2% agar was added and for methionine auxotropy determination the plates were supplemented with 50 microg/ml methionine.

Assay for Beta-galactosidase Activity

Beta-galactosidase activity was determined by a method using ortho-nitrophenyl-beta-D-galactopyranoside as enzymatic substrate. Under a specified set of conditions (temp., pH, reaction time, buffer conditions) a given amount of beta-galactosidase will degrade a certain amount of substrate and a yellow colour will be produced. The color intensity is measured at 420 nm. The measured absorbance is directly proportional to the activity of the beta-galactosidase in question under a given set of conditions.

Deletion of metE in *B. subtilis*

A plasmid /vas constructed for the purpose of deleting the metE gene in *B. subtilis*. Two flanking sequences upstream and downstream of the galE gene were amplified by PCR and fused by PCR on each side of a kanamycine (Kana) marker. This fragment was ligated in plasmid pBR322.

```
Upstream metE fragment:
P42 (SEQ ID NO: 3):
attttataggatcccgctgattcattttcttctgcgaac P43 (SEQ ID NO: 4):
gaattccatcgcactggacgacattttcaggtcgattctcggaaatcc
```

-continued

Downstream metE fragment:
P44 (SEQ ID NO: 5):
cccgaggcctttcaggcccgcaaacaatatggttgaagccgcaaaacagg P45 (SEQ ID NO: 6):
ataataatggtaccatattgatgtgacacttgaagttgc The resulting plasmid pCLO43 (SEQ ID NO: 7) was linearized and transferred to *B. subtilis* PL1801 and plated on LBPG media with 10 μg/ml kanamycine, which left the Kan marker in place of the metE gene.

A metE deletion strain designated CLO46 was tested on minimal media without mehionine. The original *B. subtilis* PL1801 (metE+) strain showed fine growth on these plates while the metE strain CLO46 showed no growth even after several days of incubation. On control minimal plates supplemented with 50 μg/ml methionine, both strains grew. The reported auxotrophic phenotype on a metE strain is therefore confirmed.

The Kan marker located in the metE locus of CLO46 was flanked by resolvase recognition sites (res), which allow a specific excision reaction in the presence of a resolvase. In order to remove the Kan marker from the chromosome, CLO46 was transformed with pWT, which is a temperature sensitive plasmid that comprises a gene coding for resolvase and an erythromycine (Erm) resistance marker. Transformants were selected on plates with 5 microg/ml Erm. They were tested for loss of the Kan marker and further re-streaked twice on plates with no antibiotics at 50° C. to cure the strains of the pVVT plasmid. Selected clones were screened for loss of Erm resistance and Kan resistance and were designated CLO49 (PL1801, metE−; no antibiotic markers).

Amplification Plasmids

An amplification plasmid was made having a transcriptional unit consisting of the gfp gene and the metE gene with a cloning site in front of the two genes, wherein a promoter could be cloned (pCLO1154, SEQ ID NO: 8). The lacZ reporter gene was also present on the plasmid expressed from a promoter separate from the promoter in front of the metE gene. Flanking these two transcriptional units was framgments from the amyE locus in *B. subtilis*.

Promoters with varying promoter activity were cloned in front of the gfp-metE transcriptional unit in the EcoRI and HindIII sites. The promoter activities spanned from 30 to 519 arbitrary units. See table 3.

TABLE 3

The table shows the promoters used in the amplification experiment and the sequence is given.

| Promoter | Activity/Units | Sequence |
|----------|---------------|----------|
| Pr30 | 30 | (SEQ ID NO: 9) |
| Pr43 | 43 | (SEQ ID NO: 10) |
| Pr119 | 119 | (SEQ ID NO: 11) |
| Pr164 | 164 | (SEQ ID NO: 12) |
| Pr342 | 342 | (SEQ ID NO: 13) |
| Pr409 | 409 | (SEQ ID NO: 14) |
| Pr519 | 519 | (SEQ ID NO: 15) |

Amplification Experiments

The resulting amplification plasmids were introduced by transformation into CLO49 (metE) and plated on solid LB media supplemented with 6 microg/ml chloramphenicol. Transformants were screened for resistance to kanamycine. Transformants being sensitive to kanamycine would have integrated part of the amplification plasmid at the amyE locus including the lacZ reporter gene and the gfp-metE operon. Those transformants would have only one copy of the genes present and they cannot be amplified.

Transformants being resistant to kanamycine would have the whole amplification plasmid integrated at the amyE locus and amplification would be possible.

Both types of transformants were plated on solid minimal TSS media without methionine. Several colonies were obtained from the transformants having the whole plasmid integrated at the amyE locus, whereas the transformants that had only part of the plasmid integrated showed no growth on minimal medium. This indicated that even with the strongest promoter, one copy of the metE gene did not express sufficient MetE protein to complement the methionine auxotrophy of the strain. However, amplification of the metE gene did result in growth of the strain.

Colonies were picked from the amplification step a long with colonies that had only one copy of the metE gene integrated in the chromosome. They were all grown in liquid LB and harvested in the exponential growth phase followed by measurement of beta-galactosidase activity. The following table gives the results from the evaluation of the amplification outcomes.

A few clones show irregular enzyme activities, which can be explained by up-mutations in the promoters.

TABLE 4

The table shows the results from the amplification trials and the beta-galactosidase activity measured in all strains after growth in LB lipuid media. The enzyme activities have been converted to the gene copy number of the reporter gene based on the enzyme activities.

| Promoter Strength | Strain | Units | Copies |
|---|---|---|---|
| 30 | 1 gene copy | 105 | 1.0 |
|  | Amplification | 1361 | 12.4 |
|  | Amplification | 218 | 2.0 |
| 43 | 1 gene copy | 101 | 0.9 |
|  | Amplification | 1467 | 13.4 |
|  | Amplification | 1460 | 13.3 |
| 119 | 1 gene copy | 113 | 1.0 |
|  | Amplification | 1055 | 9.6 |
|  | Amplification | 1075 | 9.8 |
| 164 | 1 gene copy | 102 | 0.9 |
|  | Amplification | 881 | 8.0 |
|  | Amplification | 855 | 7.8 |
| 342 | 1 gene copy | 134 | 1.2 |
|  | Amplification | 606 | 5.5 |
| 409 | 1 gene copy | 105 | 1.0 |
|  | Amplification | 533 | 4.9 |
|  | Amplification | 493 | 4.5 |
| 519 | 1 gene copy | 105 | 1.0 |
|  | Amplification | 544 | 5.0 |
|  | Amplification | 114 | 1.0 |

The results summarized herein show that it is indeed possible to increase the copy number of a chromosomally integrated expression cassette holding a weakly expressed metE gene by growing the strain on minimal medium without methionine The amplification potential >10 copies (up to 25 copies have been observed), as judged from the enzyme activities is very similar to what can be achieved by the traditional kanamycine antibiotic selection/amplification.

The invention claimed is:

1. A bacterial host cell comprising at least two copies of an amplification unit in its genome, said amplification unit comprising:
   (a) at least one copy of a gene of interest, and
   (b) an expressible conditionally essential gene, wherein the conditionally essential gene is either promoterless or transcribed from a heterologous promoter having an activity lower than the endogenous promoter of said conditionally essential gene, wherein the conditionally essential gene encodes an enzyme required for xylose, gluconate, glycerol or arabinose utilization and wherein the conditionally essential gene if not functional would render the cell auxotrophic for at least one specific substance or unable to utilize xylose, gluconate, glycerol or arabinose.

2. The cell of claim 1, wherein the bacterial host cell is a gram-positive cell.

3. The cell of claim 1, wherein the bacterial host cell is a *Bacillus* host cell.

4. The cell of claim 1, wherein the gene of interest encodes an enzyme with an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase.

5. The cell of claim 1, wherein the gene of interest encodes an antimicrobial peptide.

6. The cell of claim 1, wherein the gene of interest encodes a peptide with biological activity in the human body.

7. The cell of claim 1, wherein the amplification unit further comprises an antibiotic selection marker.

8. The cell of claim 1, wherein the amplification unit further comprises a resolvase site or res-site.

9. The cell of claim 1, wherein the conditionally essential gene is promoterless.

10. The cell of claim 9, wherein the gene of interest is located upstream of the conditionally essential gene in the amplification unit, and wherein the gene of interest and the conditionally essential gene are co-directionally transcribed.

11. The cell of claim 10, wherein the conditionally essential gene is expressed by read-through transcription from the gene of interest.

12. A method for producing a protein encoded by a gene of interest, comprising
   (a) culturing the bacterial host cell of claim 1; and
   (b) recovering the protein.

13. The method of claim 12, wherein the conditionally essential gene is at least 95% identical to a hemA sequence of *Bacillus licheniformis*.

14. The method of claim 12, wherein the conditionally essential gene is at least 97% identical to a hemA sequence of *Bacillus licheniformis*.

15. The method of claim 12, wherein the conditionally essential gene is a hemA sequence of *Bacillus licheniformis*.

16. The method of claim 12, wherein the bacterial host cell is a *Bacillus* host cell.

* * * * *